United States Patent
Deukmedjian

(10) Patent No.: US 12,239,362 B2
(45) Date of Patent: Mar. 4, 2025

(54) PAIN TREATMENT USING WANDING OF PERCUTANEOUS SURGICAL PROBE OVER SENSORY NERVE

(71) Applicant: Panacea Spine, LLC, Orlando, FL (US)

(72) Inventor: Ara Deukmedjian, Orlando, FL (US)

(73) Assignee: Panacea Spine, LLC, Orlando, FL (US)

( * ) Notice: Subject to any disclaimer, the term of this patent is extended or adjusted under 35 U.S.C. 154(b) by 0 days.

(21) Appl. No.: 18/823,628

(22) Filed: Sep. 3, 2024

(65) Prior Publication Data

US 2024/0423703 A1    Dec. 26, 2024

Related U.S. Application Data

(63) Continuation of application No. 18/767,224, filed on Jul. 9, 2024, which is a continuation-in-part of application No. 18/488,790, filed on Oct. 17, 2023.

(60) Provisional application No. 63/440,342, filed on Jan. 20, 2023.

(51) Int. Cl.
| | |
|---|---|
| *A61B 18/00* | (2006.01) |
| *A61B 18/14* | (2006.01) |
| *A61K 31/245* | (2006.01) |
| *A61K 31/445* | (2006.01) |
| *A61K 31/573* | (2006.01) |

(52) U.S. Cl.
CPC .......... *A61B 18/148* (2013.01); *A61K 31/245* (2013.01); *A61K 31/445* (2013.01); *A61K 31/573* (2013.01); *A61B 2018/0044* (2013.01); *A61B 2018/00595* (2013.01); *A61B 2018/00601* (2013.01); *A61B 2218/002* (2013.01)

(58) Field of Classification Search
CPC .......... A61B 18/00; A61B 2018/00571; A61B 2018/00577; A61B 2018/00595
See application file for complete search history.

(56) References Cited

U.S. PATENT DOCUMENTS

| | | | |
|---|---|---|---|
| 2,708,933 | A | 5/1955 | August |
| 2,828,748 | A | 4/1958 | August |
| 4,274,070 | A | 6/1981 | Thiene |
| 4,562,838 | A | 1/1986 | Walker |
| 4,781,175 | A | 11/1988 | McGreevy et al. |
| 5,254,117 | A | 10/1993 | Rigby et al. |
| 5,306,238 | A | 4/1994 | Fleenor |
| 5,312,400 | A | 5/1994 | Bales et al. |
| 5,423,760 | A | 6/1995 | Yoon |
| 5,433,739 | A | 7/1995 | Sluijter et al. |
| 6,059,781 | A | 5/2000 | Yamanashi et al. |

(Continued)

FOREIGN PATENT DOCUMENTS

WO    2022/147472 A1    7/2022

OTHER PUBLICATIONS

U.S. Appl. No. 18/767,224, filed Jul. 9, 2024; Ara Deukmedjian.
U.S. Appl. No. 18/818,398, filed Aug. 28, 2024; Ara Deukmedjian.
U.S. Appl. No. 18/819,958, filed Aug. 29, 2024; Ara Deukmedjian.

*Primary Examiner* — Deanna K Hall
(74) *Attorney, Agent, or Firm* — Gordon & Jacobson, P.C.

(57) ABSTRACT

A method of performing a rhizotomy includes directing a surgical probe through an incision in the body of a patient, navigating a distal tip of the probe to a location adjacent a target nerve, energizing the probe to deliver energy to the target nerve, and wanding the distal tip of the probe in a plurality of directions to direct the energy at the target nerve to interrupt signal transmission by the target nerve.

29 Claims, 26 Drawing Sheets

(56) References Cited

U.S. PATENT DOCUMENTS

| | | | |
|---|---|---|---|
| 6,106,524 | A | 8/2000 | Eggers et al. |
| 6,478,793 | B1 | 11/2002 | Cosman et al. |
| 7,150,747 | B1 | 12/2006 | McDonald et al. |
| 7,296,571 | B2 | 11/2007 | Foltz et al. |
| 7,429,260 | B2 | 9/2008 | Underwood et al. |
| 8,221,397 | B2 | 7/2012 | Bleich et al. |
| 8,361,067 | B2 | 6/2013 | Pellegrino et al. |
| 9,023,023 | B2 | 5/2015 | McKay et al. |
| 9,131,975 | B2 | 9/2015 | McKay |
| 9,192,438 | B2 | 11/2015 | Thiel et al. |
| 9,233,006 | B2 | 1/2016 | Assell et al. |
| 9,314,277 | B2 | 4/2016 | Assell et al. |
| 9,492,151 | B2 | 11/2016 | Bleich et al. |
| 9,981,071 | B2 | 5/2018 | McClain et al. |
| 10,058,372 | B1 | 8/2018 | Shadduck |
| 10,206,739 | B2 | 2/2019 | Godara et al. |
| 10,357,307 | B2 | 7/2019 | Harrison et al. |
| 10,463,423 | B2 | 11/2019 | Sutton et al. |
| 10,548,660 | B2 | 2/2020 | Janssen et al. |
| 10,588,691 | B2 | 3/2020 | Pellegrino et al. |
| 10,667,860 | B2 | 6/2020 | Thiel et al. |
| 10,736,688 | B2 | 8/2020 | Wright et al. |
| 10,888,371 | B2 | 1/2021 | Brustad et al. |
| 10,912,605 | B2 | 2/2021 | Solsberg et al. |
| 10,925,664 | B2 | 2/2021 | Wright et al. |
| 10,980,563 | B2 | 4/2021 | Haufe et al. |
| 11,096,738 | B2 | 8/2021 | Dinger et al. |
| 11,432,870 | B2 | 9/2022 | Schorr et al. |
| 11,590,002 | B2 | 2/2023 | Sandhu |
| 11,937,869 | B1 | 3/2024 | Deukmedjian |
| 2004/0034339 | A1 | 2/2004 | Stoller et al. |
| 2004/0181220 | A1 | 9/2004 | Farin |
| 2005/0021021 | A1 | 1/2005 | Foltz et al. |
| 2006/0036239 | A1 | 2/2006 | Canady |
| 2006/0052774 | A1 | 3/2006 | Garrison et al. |
| 2006/0069387 | A1 | 3/2006 | Gedebou |
| 2006/0178667 | A1 | 8/2006 | Sartor et al. |
| 2007/0027449 | A1 | 2/2007 | Godara et al. |
| 2008/0119846 | A1 | 5/2008 | Rioux |
| 2009/0076505 | A1 | 3/2009 | Arts |
| 2009/0228004 | A1 | 9/2009 | Kobayashi |
| 2013/0261368 | A1 | 10/2013 | Schwarts |
| 2014/0276717 | A1 | 9/2014 | Wan et al. |
| 2017/0258521 | A1 | 9/2017 | Asirvatham |
| 2018/0161088 | A1 | 6/2018 | Poser et al. |
| 2018/0206903 | A1 | 7/2018 | Podany |
| 2019/0247117 | A1 | 8/2019 | Schaning |
| 2020/0038096 | A1 | 2/2020 | Schepis et al. |
| 2020/0114041 | A1 | 4/2020 | Alas et al. |
| 2020/0188022 | A1 | 6/2020 | Mingione |
| 2020/0390496 | A1 | 12/2020 | Houden et al. |
| 2022/0241000 | A1 | 8/2022 | Newman et al. |
| 2022/0401027 | A1 | 12/2022 | Mowery et al. |
| 2024/0245477 | A1 | 7/2024 | Deukmedjian |
| 2024/0245488 | A1 | 7/2024 | Deukmedjian |
| 2024/0307105 | A1 | 9/2024 | Nolan et al. |

PAIN TREATMENT USING WANDING OF PERCUTANEOUS SURGICAL PROBE OVER SENSORY NERVE

CROSS-REFERENCE TO RELATED APPLICATIONS

This application is a continuation of U.S. Ser. No. 18/767,224, filed Jul. 9, 2024, which is a continuation-in-part of U.S. Ser. No. 18/488,790, filed Oct. 17, 2023, which claims benefit of U.S. Provisional App. No. 63/440,342, filed Jan. 20, 2023, all of which are hereby incorporated by reference herein in their entireties.

TECHNICAL FIELD

This document relates generally to thermal ablation systems and methods, including but not limited to, improved systems and methods for performing rhizotomies.

BACKGROUND

As a result of injury or the aging process, joints can become painful. The pain from a joint is worsened with movement of the joint. Chronic pain is most often the result of an overactive sensory nerve at the injured joint. One manner of treating joints suffering chronic pain includes thermal ablation.

Thermal ablation involves the creation of temperature changes sufficient to produce necrosis in a specific target tissue within a patient and, in this case, particularly at the joint. The target tissue for treatment of joint pain is the sensory nerve. A significant challenge in ablation therapy is to provide adequate treatment to the targeted tissue while sparing the surrounding tissue structures from injury. An additional challenge with common ablation procedures and associated medical devices is that the effect of the treatment is temporary, e.g., lasting between six to twelve months and must be repeated for longer term pain relief.

Thermal ablation can be carried out using radio-frequency (RF) energy. This type of thermal ablation, also referred to as RF ablation, uses electrical energy transmitted into a target volume through an electrode to generate heat in the area of the electrode tip. The radio waves emanate from a non-insulated distal portion of the electrode tip. The introduced radiofrequency energy causes molecular strain, or ionic agitation, in the area surrounding the electrode as the current flows from the electrode tip to ground. The resulting strain causes the temperature in the area surrounding the electrode tip to rise.

At least some current ablation procedures employ an elongated RF needle that is inserted percutaneously and navigated to a location adjacent a target nerve. In various procedures, access to a target nerve may be limited (e.g., limited to a restricted angular range) and/or locating the probe in close proximity to the nerve may only be roughly approximated, thereby raising significant challenges in directing the field generated by the probe at the target nerve to provide optimal clinical outcomes. Additionally, anatomical variations of the nerve location relative to anatomical landmarks can compound the issue of locating and ablating the nerve of interest.

For example, a known rhizotomy procedure uses a small needle directed to the nerves at a facet joint between vertebrae. The needle is very flexible, and is inserted to a pinpoint target using a stylus. The stylus may be removed and then the energy may be applied at the pinpoint target to ablate the tissue around the needle point. However, the location of targeted nerves can vary from patient-to-patient, making it difficult to conclude with certainty that the pinpoint target includes the nerves to be ablated. Another problem with known rhizotomy procedures is that the needle needs to be removed and reinserted into the patient to a different pinpoint target to target a different nerve.

SUMMARY

A probe is employed for transecting a target nerve in a rhizotomy procedure. Transecting includes cutting to section and/or dividing. The probe has sufficient size, rigidity, and power output to be operated in a percutaneous manner. The probe is advanced percutaneously through a small incision to the target nerve.

The probe may be an electrocautery probe, a laser probe, a mechanically abrasive probe, chemical delivery probe, a cryogenic cooling probe, ultrasonic energy delivery probe, microwave energy probe, or other energy or stimulation delivery probe activatable for carrying out ablation and/or transection of the target nerve in the rhizotomy procedures described herein.

With reference to an electrocautery probe, the method has a number of advantages over methods employing typical RF ablation. The electrocautery probe has an increased size, rigidity, and power output relative to prior RF ablation tools. Ablation includes thermally burning. In the present disclosure, the electrocautery probe is adapted to sufficiently ablate the nerve to transect the nerve.

Methods using the probes described herein have improved clinical outcomes. The surgeon moves the distal tip of the probe while the probe is energized and proximate the target nerve. This increases the likelihood the nerve will be efficaciously affected by the energy delivered by the probe. The probe is preferably "wanded" (e.g., operated like wand) to displace the distal tip throughout a wanded area, i.e., about various locations in and above a surface area where the target nerve is expected to be. For some joints, the wanded area may be in the range of 50-1000 $mm^2$; for other joints the wanded area may be significantly smaller, and as small as 10 $mm^2$. In all cases, the wanded area is larger than the treatment areas of standard RF needle probe ablation, which is typically approximately no more than 4 $mm^2$. Additionally, the increased size and power output of the electrocautery probe described herein delivers energy to a larger field or zone of tissue. Further, the probe and tip have a sufficiently small size such that it can be advanced percutaneously and navigated to the treatment location under imaging.

By way of example, a dorsal ramus rhizotomy procedure may be performed by wanding the tip of the probe along vertebrae near a facet joint where the dorsal ramus is expected to be. For example, the tip of the probe may be moved along the transverse process to the pedicle to ablate and optimally transect the medial branch of the dorsal ramus adjacent the facet joint.

The effect of these advantages of employing an electrocautery probe in, e.g., a dorsal ramus rhizotomy may be to denervate the target nerve for a longer period of time and potentially permanently in the case the probe transects the target nerve preventing it from regenerating over time. When the target nerve is destroyed, pain at the joint is reduced and movement of the joint is facilitated. Joint movement promotes an active and healthy lifestyle.

An example (e.g., "Example 1") of a method for performing a rhizotomy may include creating an incision in a body of a patient, directing a probe percutaneously through the incision, navigating a distal tip of the probe to a location adjacent a target nerve, activating the probe to deliver energy to the target nerve, and moving the distal tip of the probe in a plurality of directions while the probe is energized to direct the energy at the target nerve.

In Example 2, the probe may be an electrocautery probe.

In Example 3, the subject matter of any one of Examples 1-2 may optionally be configured such that the incision in the body of the patient is made with the energized electrocautery probe.

In Example 4, the subject matter of Examples 1-3 may optionally be carried out with the probe navigated through the incision to the location adjacent the target nerve and in the plurality of directions under imaging; such imaging may be via fluoroscopy.

In Example 5, the subject matter of any of Examples 1-4 may optionally be carried out such that the plurality of directions be in three dimensions. In Example 5, it is preferred that the probe be moved along a boney surface, as well as above the boney surface, in the location adjacent a joint capsule.

In Example 6, the subject matter of any of Examples 1-5 may optionally be carried out such that movement of the energized probe operates to transect the target nerve.

In Example 7, the subject matter of any of Examples 1-6 is carried out to target a sensory branch nerve immediately outside the joint before the nerve enters the joint capsule to innervate the joint.

In Example 8, the subject matter of any one of Examples 1-7 may optionally be configured such that the boney surface includes a vertebra of a spine.

In Example 9, the subject matter of Example 8 may optionally be configured such that the vertebra includes vertebra in a lumbar region of the spine.

In Example 10, the subject matter of Example 8 may optionally be configured such that the vertebra includes vertebra in a cervical region of the spine.

In Example 11, the subject matter of Example 8 may optionally be configured such that the vertebra includes vertebra in a thoracic region of the spine.

In Example 12, the subject matter of any one of Examples 1-11 may optionally be carried out such that the target nerve is a medial branch of a dorsal ramus that passes along a transverse process to innervate a facet joint in a spine, and moving the distal tip includes wanding the distal tip along the transverse process to a pedicle to ablate, and more preferably transect, the medial branch of the dorsal ramus.

In Example 13, the subject matter of Example 12, the target nerve is ablated and more preferably transected at a location between a root of the nerve and a facet joint synovium; ablation preferably occurs outside of the facet joint synovium.

In Example 14, the subject matter of any of Examples 1-6 may optionally be carried out such that the target nerve is a nerve that runs along a sacrum.

In Example 15, the subject matter of any of Examples 1-6 may optionally be carried out such that the target nerve is a nerve that runs along a sacroiliac joint.

In Example 16, the subject matter of any one of Examples 1-15 may optionally be carried out such that moving the distal tip of the probe comprises moving the distal tip laterally, medially, rostrally, caudally, and/or along a facet joint.

In Example 17, the subject matter of any one of Examples 1-15 may optionally be carried out such that moving the distal tip of the probe comprises moving the distal tip laterally-to-medially and/or medially-to-laterally.

In Example 18, the subject matter of any one of Examples 1-15 may optionally be carried out such that moving the distal tip of the probe comprises moving the distal tip of the probe rostrally-to-caudally and/or caudally-to-rostrally.

In Example 19, the subject matter of any one of Examples 1-6 may optionally be carried out such that the target nerve is a sensory nerve innervating a joint of an extremity, and moving the distal tip includes causing the distal tip to transect the nerve.

In Example 20, the subject matter of any one of Examples 1-6 may be carried out such that the target nerve is a sensory nerve innervating a shoulder joint.

In Example 21, the subject matter of Example 20 may be carried out such that the target nerve includes one or more of the following sensory nerves: an articular branch of the suprascapular nerve, an articular branch of the axillary nerve, an articular branch of the lateral pectoral nerve, and an articular branch of the subscapular nerve.

In Example 22, the subject matter of Example 20 may be carried out such that the probe is moved along a honey surface comprising a posterior neck of a scapula at a base of a glenoid extending in a superior-to-inferior and/or interior-to-superior direction, and lateral to a spinoglenoid notch.

In Example 23, the subject matter of any one of Examples 1-6 may be carried out such that the target nerve is a sensory nerve innervating a sacroiliac joint.

In Example 24, the subject matter of Example 23 may be carried out such that the target nerve includes at least one of the dorsal ramus branch nerves extending between the S1, S2, S3 and S4 posterior foramen and the sacroiliac joint they innervate; and the L5 dorsal ramus nerve.

In Example 25, the subject matter of Example 23, carried out such that the probe is moved along at least one of a sacrum lateral to the S1, S2, S3 and S4 posterior foramen towards a sacroiliac joint between the posterior foramen and the sacroiliac joint they innervate; and a posterior sacrum.

In Example 26, the subject matter of any one of Examples 1-6 may be carried out such that the target nerve is a sensory nerve innervating the hip joint.

In Example 27, the subject matter of Example 26 is configured such that the target nerve includes one or more of the following sensory nerves: an articular branch of the femoral nerve, an articular branch of the obturator nerve, an articular branch of the superior gluteal nerve, and an articular branch of the nerve to the quadratus femoris.

In Example 28, the subject matter of Example 26, carried out such that the probe is moved along a boney surface comprising at least one of a bone surface inferomedial to the anterior inferior iliac spine along the superior rim of the acetabulum exterior to a joint capsule; the bone surface at the junction of the pubic and iliac bones in the region of the "teardrop," as well as the bone surface immediately inferior to the teardrop; and posterior along the acetabulum proximal to the joint labrum.

In Example 29, the subject matter of any one of Examples 1-6 may be carried out such that the target nerve is a sensory nerve innervating the knee joint.

In Example 30, the subject matter of Example 29 is configured such that the target nerve includes one or more of the following sensory nerves: a superolateral genicular nerve, a superomedial genicular nerve, and an inferomedial genicular nerve.

In Example 31, the subject matter of Example 29, carried out such that the probe is moved along a bone surface comprising at least one of a junction of a femoral shaft and a lateral femoral condyle; a junction of the femoral shaft and a medial femoral condyle; and a tibial shaft and a medial tibial tubercle.

In Example 32, the subject matter of any one of Examples 1-31 may optionally be configured such that the probe comprises shovel shaped distal tip.

In Example 33, the subject matter of Example 31 may optionally be configured such that the shovel shaped distal tip comprises a blunt curved distal end.

In Example 34, the subject matter of Example 31 may optionally be configured such that the shovel shaped distal tip comprises a beveled surface.

In Example 35, the subject matter of Example 34 may optionally be configured such that navigating the distal tip comprises employing the beveled surface of the distal tip to turn the distal tip away from the beveled surface.

In Example 36, the subject matter of any one of Examples 1-35 may optionally be configured such that the distal tip of the probe comprises a cross-section having a major dimension that is greater than approximately 3 millimeters (0.118 inches).

In Example 37, the subject matter of any one of Examples 1-35 may optionally be configured such that the distal tip of the probe has a shaft with a diameter between 3 mm and 6 mm.

In Example 38, the subject matter of any one of Examples 1-35 may optionally be configured such that the distal tip of the probe has a shaft with a diameter between 3 mm and 5 mm.

In Example 39, the subject matter of any one of Examples 1-38 may optionally be configured such that a portion of the probe adjacent the distal tip is at least partially covered with a guard.

In Example 40, the subject matter of Example 39 may optionally be configured such that the guard comprises a polymer.

In Example 41, the subject matter of any one of Examples 39-40 may optionally be configured such that the guard is formed from a material to resist deformation from heat and motion during when the probe is energized and the distal tip is moved.

In Example 42, the subject matter of any one of Examples 39-41 may optionally be configured such that the guard has a tapered end to resist deformation from motion.

In Example 43, the subject matter of any one of Examples 39-42 may optionally be configured such that the distal tip includes exposed metal with a length of between 3 mm to 7 mm beyond the guard.

In Example 44, the subject matter of any one of Examples 1-43 may optionally be configured such that the probe includes a shaft with the distal tip, wherein the distal tip is tapered.

In Example 45, the subject matter of any one of Examples 1-44 may optionally be configured such that the probe includes a shaft with an electrical conductor for delivering electrical energy to the distal tip when the probe is energized, wherein the moving the distal tip includes wanding the shaft of the probe while energizing the probe, wherein the shaft is sufficiently stiff to resist deformation when the shaft is wanded to move the distal tip of the probe.

In Example 46, the subject matter of Example 45 may optionally be configured such that the electrical conductor enables the shaft to be sufficiently stiff to resist deformation.

In Example 47, the subject matter of any one of Examples 1-46 may optionally be configured such that energizing the probe comprises energizing the probe in a range over 100 Watts.

In Example 48, the subject matter of any one of Examples 1-47 may optionally be configured such that energizing the probe comprises energizing the probe to a temperature over 100 C.

In Example 49, the subject matter of any one of Examples 1-48 may optionally be configured such that energizing the probe comprises energizing the probe to a temperature within a range between 150 C and 1250 C.

In Example 50, the subject matter of Example 49 may optionally be configured such that energizing the probe comprises energizing the probe to a temperature within a range between 250 C and 1000 C.

In Example 51, the subject matter of any one of Examples 1-50 may optionally be configured such that energizing the probe comprises energizing the probe with sufficient energy to coagulate or vaporize without charring tissue.

In Example 52, the subject matter of any one of Examples 1-51 may optionally be configured such that energizing the probe comprises energizing the probe to deliver RF energy to the target nerve for a time period in a range from approximately 5 seconds to approximately 10 seconds.

In Example 53, the subject matter of any one of Examples 1-52 may optionally be configured to further include navigating a needle to the location adjacent the target nerve, and delivering medicine through the needle to the location adjacent the target nerve.

In Example 54, the subject matter of Example 53 may optionally be configured such that the medicine comprises at least one of a local anesthetic and an anti-inflammatory medicine.

In Example 55, the subject matter of Example 54 may optionally be configured such that the medicine comprises at least one of novocaine or procaine (Novocain), bupivacaine (Marcaine), and methylprednisolone (Depo-Medrol).

In Example 56, the subject matter of Example 45 may optionally be configured such that the medicine comprises a combination of novocaine, bupivacaine, and methylprednisolone.

In Example 57, the subject matter of any one of Examples 1-53 may optionally be configured such that the probe is cannulated having a lumen extending along a longitudinal axis of the probe from near a proximal end to near the distal tip.

In Example 58, the subject matter of Example 57 may optionally be configured to further include delivering medicine through the lumen of the cannulated probe to the location adjacent the target nerve.

In Example 59, the subject matter of Examples 58 may optionally be configured such that the medicine comprises at least one of a local anesthetic and an anti-inflammatory medicine.

In Example 60, the subject matter of Example 59 may optionally be configured such that the medicine comprises at least one of novocaine, bupivacaine, and methylprednisolone.

In Example 61, the subject matter of Example 60 may optionally be configured such that the medicine comprises a combination of novocaine, bupivacaine, and methylprednisolone.

In Example 62, the subject matter of either Examples 53 or 57 may optionally be configured such that the target nerve is a medial branch of the dorsal ramus.

In Example 63, the subject matter of Example 62 may optionally be configured such that the target nerve is the medial branch of the dorsal ramus at a cervical, thoracic and lumbar vertebrae.

In Example 64, the subject matter of Example 63 may optionally be configured such that the target nerve is the medial branch of the dorsal ramus at or adjacent one of the C2-3 through the L5-S1 facet joints.

In Example 65, the subject matter of Examples 53 or 57 may optionally be configured such that the location adjacent the target nerve comprises a junction of a transverse process, a pedicle, and superior facet.

In Example 66, the subject matter of any of Examples 53 or 57 may optionally be configured such that the that the location adjacent the target nerve comprises a location targeting the sensory nerves innervating the shoulder joint.

In Example 67, the subject matter of Example 66 is carried out such that the location adjacent the target nerve targets at least one of the following nerves: an articular branch of the suprascapular nerve, an articular branch of the axillary nerve, an articular branch of the lateral pectoral nerve, and an articular branch of the subscapular nerve.

In Example 68, the subject matter of Example 66 is carried out such that the location adjacent the target nerve is along a posterior neck of a scapula at a base of a glenoid extending in a superior-to-inferior, and/or interior-to-superior, direction, and lateral to a spinoglenoid notch.

In Example 69, the subject matter of any of Examples 53 or 57 may optionally be configured such that the that the location adjacent the target nerve comprises a location targeting the sensory nerves innervating the sacroiliac joint.

In Example 70, the subject matter of Example 69 is carried out such that the location adjacent the target nerve targets at least one of the following nerves: the dorsal ramus branch nerves extending between the S1, S2, S3 and S4 posterior foramen and the sacroiliac joint they innervate and the L5 dorsal ramus nerve.

In Example 71, the subject matter of Example 69 is carried out such that the location adjacent the target nerve is along at least one of a sacrum lateral to the S1, S2, S3 and S4 posterior foramen towards a sacroiliac joint between the posterior foramen and the sacroiliac joint they innervate; and a posterior sacrum.

In Example 72, the subject matter of any of Examples 53 or 57 may optionally be configured such that the that the location adjacent the target nerve comprises a location adjacent a sensory nerve innervating the hip joint.

In Example 73, the subject matter of Example 72 is carried out such that the location adjacent the target nerve is adjacent one of the following nerves: an articular branch of the femoral nerve, an articular branch of the obturator nerve, an articular branch of the superior gluteal nerve, and an articular branch of the nerve to the quadratus femoris.

In Example 74, the subject matter of Example 72, carried out such that the location adjacent the target nerve is at least one (i) along the bone inferomedial to the anterior inferior iliac spine along the superior rim of the acetabulum exterior to the joint capsule, (ii) along the bone surface at the junction of the pubic and iliac bones in the region of the "teardrop" as well as the bone surface immediately inferior to the teardrop, (iii) posterior along the acetabulum proximal to the joint labrum.

In Example 75, the subject matter of any of Examples 53 or 57 may optionally be configured such that the that the location adjacent the target nerve comprises a location adjacent a sensory nerve innervating the knee joint.

In Example 76, the subject matter of Example 75 is carried out such that the location adjacent the target nerve is adjacent one of the following nerves: a superolateral genicular nerve, a superomedial genicular nerve, and an inferomedial genicular nerve.

In Example 77, the subject matter of Example 75, carried out such that the location adjacent the target nerve is at least one (i) a junction of a femoral shaft and a lateral femoral condyle, (ii) a junction of the femoral shaft and a medial femoral condyle, and (iii) a tibial shaft and a medial tibial tubercle.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following description of the present subject matter refers to the accompanying drawings which show, by way of illustration, specific aspects, and embodiments in which the present subject matter may be practiced. These embodiments are described in sufficient detail to enable those skilled in the art to practice the present subject matter. Other embodiments may be utilized, and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

In addition, the drawings depicting anatomy are not intended to be true depictions of the target nerves, underlying bone structure, and surrounding anatomy. Rather, the drawings are meant to be mere representations of the type of treatment that can be performed in both general and specific locations, and particularly at referenced joints. The drawings should not be relied upon for the exact or approximate size, shape or location of treatment areas in relation to the target nerves.

Figure 1:
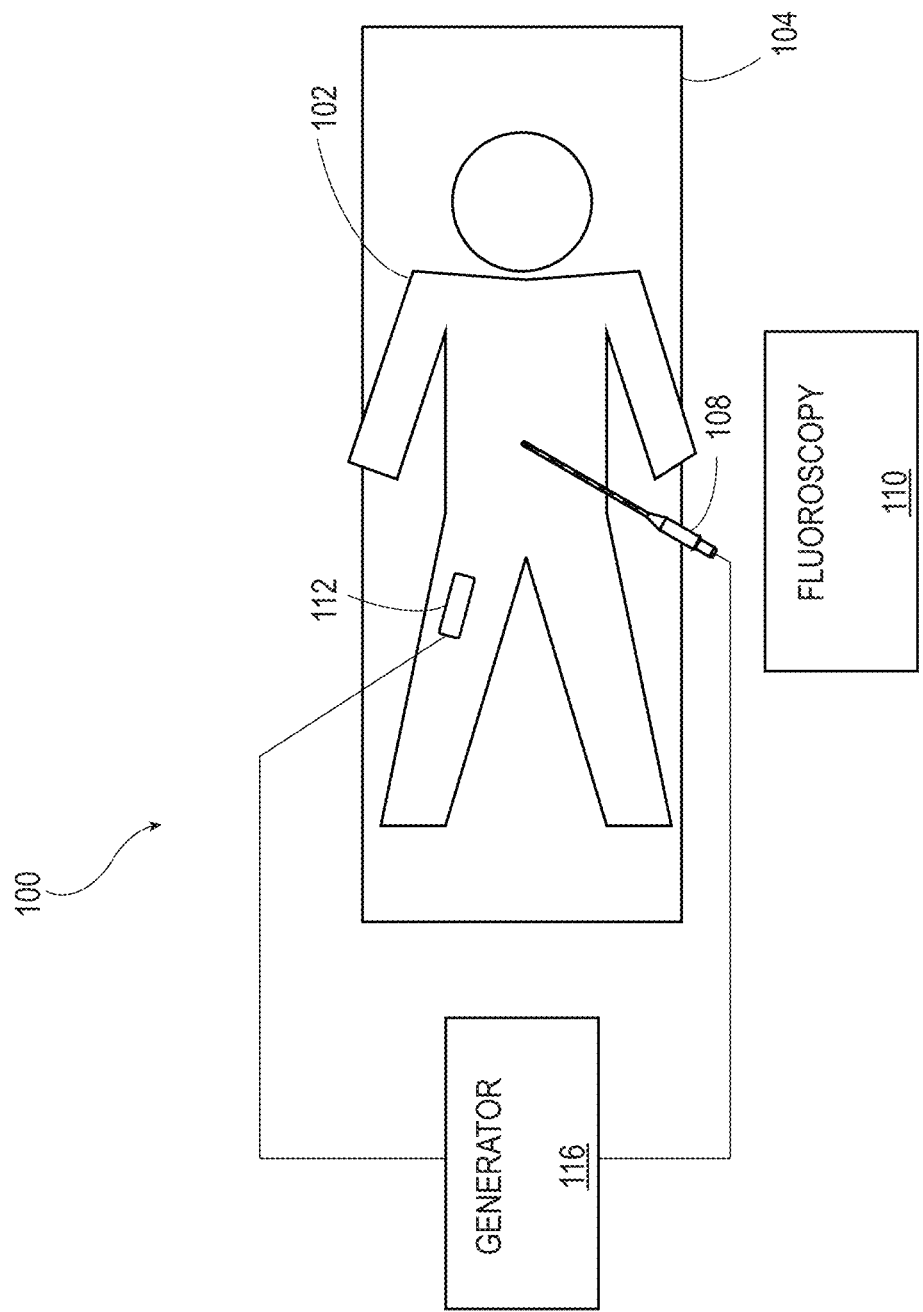
FIG. 1 is a schematic depicting an example medical system in accordance with the present disclosure.

FIG. 1 is a schematic depicting an exemplar medical system 100 in accordance with the present disclosure. The system 100 can be employed in a variety of procedures, including, for example, in a rhizotomy. In examples, the system 100 is employed in a dorsal ramus rhizotomy. In an example dorsal ramus rhizotomy, a patient 102 can be positioned face down on the table 104 to allow access along the spine of the patient. The table 104 may be made of radiolucent materials substantially transparent to x-rays.

System 100 includes an energy generator 106, a treatment probe 108, and a fluoroscopy system 110. The energy generator 106 in an embodiment is an electrosurgical generator 106, and the probe 108 is an embodiment an electrocautery probe. The generator 106 may be electrically connected to the probe 108. The fluoroscopy system 110 may include a number of different types of fluoroscopy systems/devices, including, for example an intraoperative X-ray system configured to produce multiple orthogonal views of the anatomy of patient 102. For example, the fluoroscopy system 110 may include an intraoperative X-ray system configured to produce anterior-posterior, lateral, and oblique views.

Figure 2:
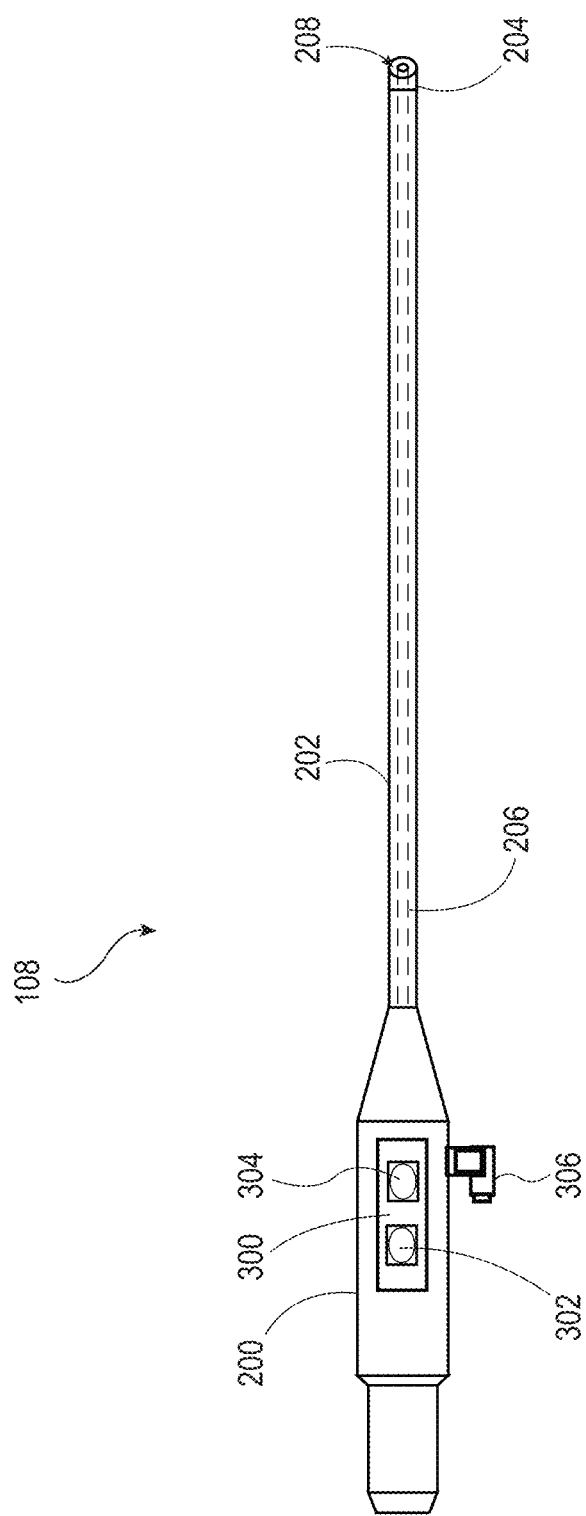
FIG. 2 is a schematic depicting an example electrocautery probe in accordance with this disclosure.

The generator 106 may be a variety of different types of electric generators that are configured to generate energy this is delivered through the probe 108 to patient tissue. The generator 106 may be configured to generate energy delivered through the probe 108 in the radio frequency band, e.g., in a frequency range from approximately 450-500 kHz. The generator 106 may also be configured for closed-loop control of the energy emanating from the electrocautery probe 108 based on, e.g., temperature. For example, the probe 108 may include a temperature sensor, e.g., a thermocouple, to measure the temperature at/around the site within the body of the patient 102 that is the target of the treatment. The generator 106 may receive measurements from the temperature sensor and control energy output based the desired temperature for the electrocautery procedure. Data may also be available from the generator 106, e.g., power level and/or impedance, which may also be used for closed-loop control of the probe 108. The generator 106 and the probe 108 may be configured to operate at and deliver variable energy. In this manner they can be optimized to perform cutting at a relatively higher first power and/or first waveform and coagulation at a relatively lower second power and/or second waveform. Alternatively, a combination of simultaneous cutting and coagulation can be achieved via a variable power and/or a variable waveform, which limits blood loss during cutting. The probe includes or is coupled to user input controls (e.g., buttons, thumb/finger wheels, foot pedals, etc.) for operation of the probe 108, including, e.g., for activating electrical energy generated by generator 106 and delivered through the probe 108 and an electrode at the distal tip 204 (FIG. 2).

The generator 106 and the electrocautery probe 108 are typically configured for monopolar energy delivery to the target site within the patient 102. However, systems may be designed for bipolar energy delivery. In instances where the probe 108 is monopolar, a return electrode pad 112 may be attached to patient 102 to complete a circuit from the generator 106, through the probe 108, through a portion of the patient 102, and back to the generator 106 through the return electrode 112. In bipolar arrangements, the electrocautery probe may include at least one supply and at least one return electrode to define the electrical circuit that transmits energy to the target site within patient 102. While an RF energy generator is preferred, another energy generator suitable to apply energy at the tip that permits the tip to transect the target nerve can also be used. One suitable electrosurgical generator 106 is the ValleyLab Force 2 electrosurgical generator.

In other embodiments, the generator may be a microwave generator, an ultrasonic energy generator, a mechanical energy generator, a laser energy generator, a cryofluid circulating system or other cryocooling system, a heater, a chemical delivery pump, or other suitable generator. In such case, when the generator is operated and the probe is activated, energy is delivered through the distal tip of the probe to effect a modulation of the target nerve that interrupts and/or permanently destroys transmission of the pain signal through the target sensory nerve. Each type of generator may have an associate distal tip for delivery of the generated microwave, ultrasonic or laser energy, for heat transfer, for mechanical tissue abrasion and/or for chemical delivery.

While prior rhizotomies are commonly performed with a small, flexible RF ablation needle at relatively lower ablation energies, the electrocautery probe 108 for conducting energy to the target location is specifically adapted to deliver higher energies to target nerves, e.g., the medial branch of the dorsal ramus at the C2-3 through L5-S1 facet joints, and the sensory nerves at the sacroiliac joint, the shoulder, hip, and knee joints as described hereinbelow, all treatment locations by way of example only. Employing the electrocautery probe 108 can provide a number of advantages over employing a typical RF ablation needle. The increased size and power output of the electrocautery probe can facilitate improved clinical outcomes by allowing the surgeon to move the distal tip of the probe in vivo adjacent the approximated location of the target nerve, which increases the likelihood the nerve will be efficaciously affected by the RF energy delivered by the probe. Efficacious therapeutic effect preferably includes transecting the nerve, i.e., cutting through the both the epinerium and perinerium connective tissue layers surrounding the nerve fibers within a nerve, such that the cauterized nerve is permanently prevented from regrowth. Additionally, the increased size and power output of the electrocautery probe delivers a larger field or zone of affected tissue when the probe is energized. Further, the probe and its distal tip can be moved through tissue and along nerves while energized.

In some examples, the generator 106 is configured to energize the probe 108 using power in a range from approximately 20 Watts to approximately 60 Watts. In some examples, the generator 106 is configured to energize the electrode using power in a range from approximately 20 Watts to approximately 100 Watts. In some examples, the generator 106 is configured to energize the electrode using power over 100 Watts. In some examples, the generator 106 is configured to energize the electrode to be heated to a temperature over 100 C. In some examples, the temperature is within a range between 150 C and 1250 C. In some examples, the temperature is within a range between 250 C and 1000 C.

FIG. 2 is a schematic depicting one exemplar probe 108 in accordance with this disclosure. The probe 108 may include a handle 200, a shaft 202, a distal tip 204, and optionally a lumen 206. In addition, the probe may be fluidically connected to a source of medication or other therapeutic agent which can be then be delivered through lumen 206. As such, the probe 108 provides a single device that can deliver medication and energy to the target site.

The handle 200 may include user input controls 300. The input controls 300 may include separate buttons 302, 304 or other actuators for different energy application for cutting and/or coagulation. The handle 200 may also include the fluid connector 306, e.g., in the form of Luer connector.

Figure 3A:
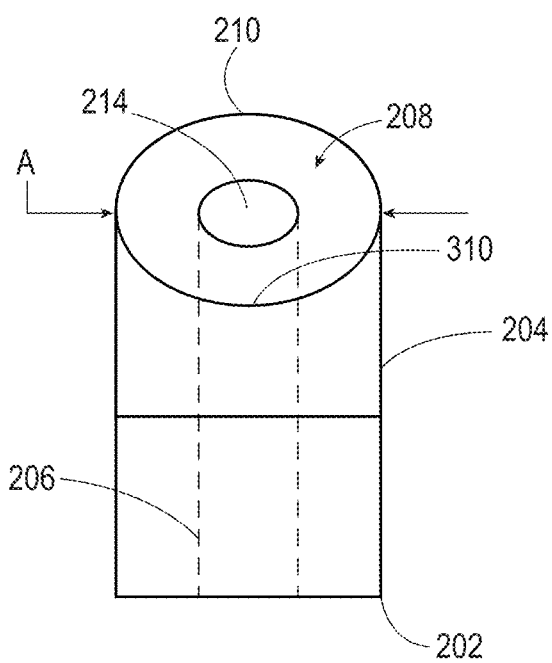
FIGS. 3A and 3B are schematics depicting the distal tip of the example electrocautery probe of FIG. 2.
Figure 3B:
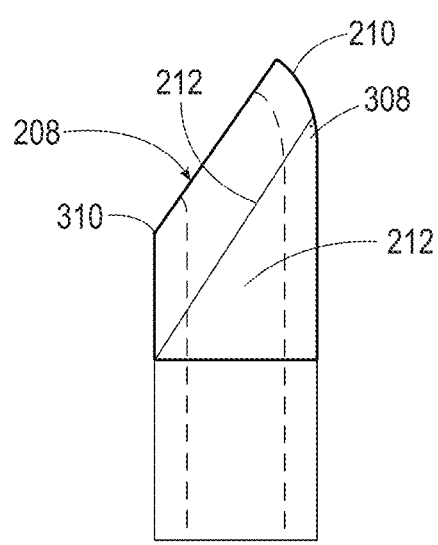

Referring to FIGS. 2, 3A and 3B, the shaft 202 may include multiple sheaths, catheters, etc. to form the elongated shaft that is navigated through the patient's anatomy to place the distal tip 204 and associated electrode(s) at the target location within the patient. For example, the shaft 202 may include an outer sheath/guard layer 212 that surrounds the lumen 206 and an elongated electrical connection to the electrode(s) at the distal tip 204. The outer sheath/guard layer of the shaft 202 may be made from polyether ether ketone (PEEK), which provides insulation to the covered portion of the probe and enhances rigidity. The guard/outer sheath 212 can extend toward the end 210 of the distal tip 204. In an example, the distal end 308 of the guard 212 can extend toward the end 210 opposite the beveled surface 208, and optionally beyond one or both of a proximal surface 310 of the beveled surface 208 and the opening of the lumen 206. Additionally, the lumen 206 may terminate at beveled surface 208 such that the lumen defines an aperture 214 in the beveled surface 208. In some embodiments, a length of exposed metal beyond the guard (insulator) may be within a range from about 3 mm to 7 mm beyond the electrical insulator.

The distal tip 204 of the probe 108 includes or defines one or more electrodes or treatment ends by which energy can be delivered to a target site, i.e., a sensory nerve. In examples, distal tip 204 of an electrocautery probe has a shovel shape with a beveled surface 208. The shovel shaped distal tip 204 defines a curved distal end 210 and can include/define an elliptical or oblate shape. The shape of distal tip 204 can have a number of benefits in procedures in which probe 108 can be used, including, by way of example and not limitation, dorsal ramus rhizotomies. The distal tip is appropriately shaped, to permit puncture, incision, and percutaneous insertion of the probe through tissue to a location on a boney surface adjacent a target nerve while the probe is energized. The shovel shaped curved end 210 in combination with the beveled surface 208 may improve navigation through the patient's anatomy to the target location by allowing the distal tip 204 of the probe 108 to turn without inadvertently digging into, puncturing, cutting or otherwise being entangled with tissue. Additionally, the shovel shaped beveled surface 208 may assist in better steering electrical energy in a desired direction and may increase the surface area of the electrode by which such energy is delivered.

The distal tip 204 of the electrocautery probe 108 may include a cross-section having a major dimension A that is approximately 3 millimeters is size, or greater than 3 millimeters (0.118 inches). The increased size of the distal tip 204 and associated increased surface area improved by beveled surface 208 can allow probe 108 to deliver more energy to a larger area/zone at the target location within the patient, which, in turn, can improve clinical outcomes of procedures conducting using the probe.

Turning now to FIGS. 26 through 29, another embodiment of an electrocautery probe 1108 is shown. The probe 1108 includes rigid shaft 1202, a metal tip 1204 at a distal end 1203 of the shaft that is adapted to cut when energized, and a proximal end 1205. An electrode 1216 extends through the shaft into electrical communication with the distal tip 1204 and also preferably protrudes from the proximal end 1205. The shaft 1202 includes an external insulated guard or barrier material 1212, as described above, about the electrode 1216. The distal tip 1204 preferably extends from a center of the distal end 1203 of the shaft 1202. The shaft 1202 is preferably a unitary body from the proximal end 1205 to the distal end 1203. The shaft 1202 smoothly tapers to the distal end 1203 without any interruption, protrusion, shoulder structure, or shrink wrap material than could catch on tissue; that is, it is preferred that the distal portion of the shaft have a smooth surface profile to aid in tissue insertion.

In an embodiment, the metal tip 1204 has a length of 4.3 mm (0.17 inch), a thickness of 0.5 mm (0.02 inch) at where it extends from the shaft 1202, and tapers over a distal 3.0 mm (0.12 inch) portion of its length; the tip has a width of 2.3 mm (0.09 inch), and has a radius of 1.14 mm (0.045 inch) forming a semicircular tapered distal edge 1210. Each of the foregoing dimensions can also optimally be varied in a range of ±20%. The distal tip 1204 is sharp in a direction transverse to the radiused edge 1210, and stiff, adapted to not bend under normal use.

Referring back to FIG. 26, a handpiece or handle 1200, preferably adapted to be removable from the shaft at the electrode 1216, is couplable at the proximal end 1205 of the shaft 1202. The handle 1200 includes actuation controls 1300 (e.g., to trigger one of coagulation or cutting RF energy to be applied from the RF generator to the distal cutting tip 1204) and electrical connection (not shown) to the RF generator. The shaft 1202 is preferably a single use, disposable device, whereas the handle 1200 may be reusable.

Figure 28:
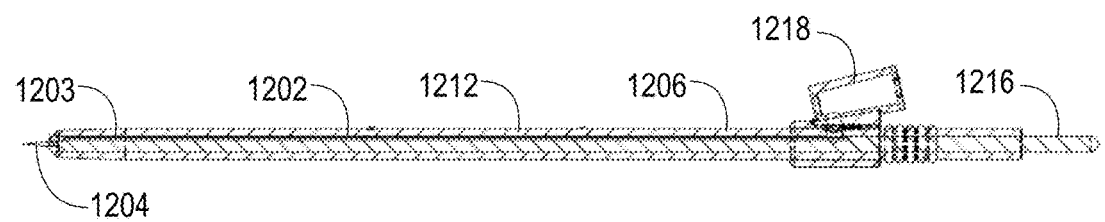
FIG. 28 is a longitudinal section across the cautery device of FIG. 27.
Figure 29:
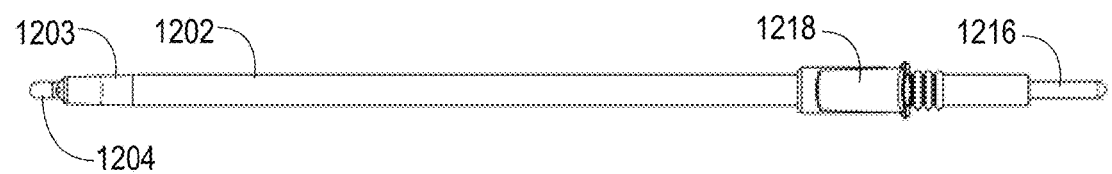
FIG. 29 is a top view rotated 90° from the side elevation of FIG. 27.
Figure 30:
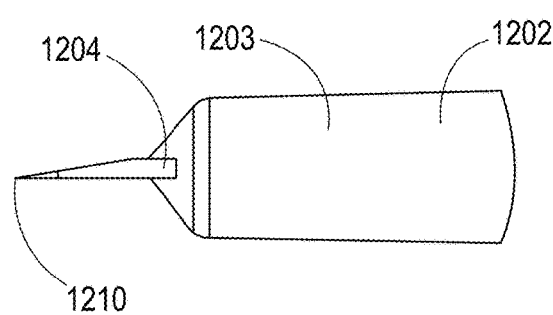
FIG. 30 is an enlarged distal end side view of the distal tip of the cautery device of FIG. 27.
Figure 31:
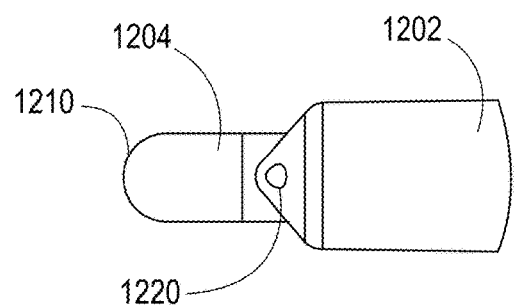
FIG. 31 is an enlarged distal end of the cautery device of FIG. 27, rotated 90° relative to FIG. 30.
Figure 32:
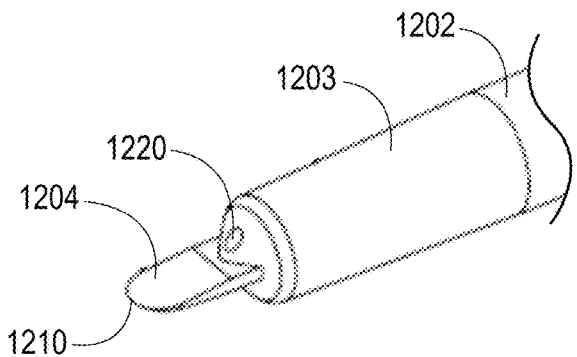
FIG. 32 is an enlarged perspective view of the distal end of the cautery device of FIG. 27.
Figure 33:
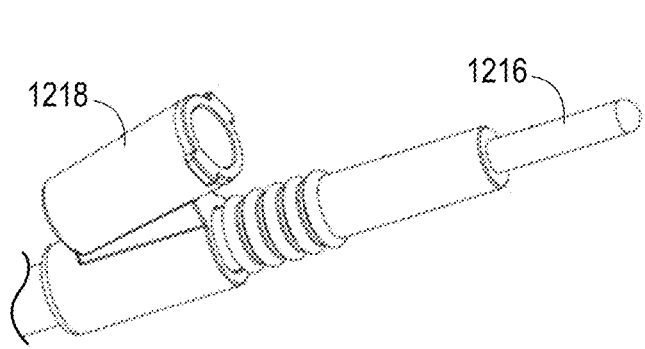
FIG. 33 is an enlarged perspective view of the proximal end of the cautery device of FIG. 27.
Figure 34:
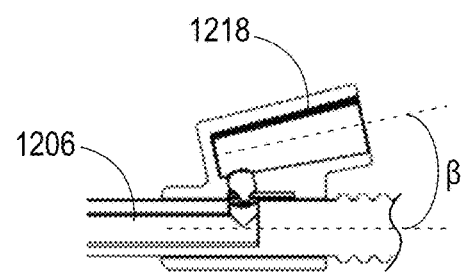
FIG. 34 is an enlarged longitudinal section view of proximal end of the cautery device.

Referring to FIG. 28, a fluid lumen 1206 extends through the shaft 1202, preferably parallel to the electrode 1216. The distal end 1203 of the shaft 1202 includes a tapered portion 1230 that is adapted to interference fit within a female Luer connector to make a substantially fluid tight connection. More particularly, the tapered portion is preferably tapered at a Luer taper angle of 1.72°; however, based on material tolerances, tapers outside of the standard Luer taper angle and in a range of 0.5-6° may be suitable to effect sufficient interference for a fluid tight interference fit.

Referring to FIGS. 26 through 29 and 32 through 34, the proximal portion of the shaft includes a syringe connector 1218, preferably in the form of female Luer connector. The syringe connector 1218 is in fluid communication with the lumen 1206, which has an exit 1220 at the tapered distal portion 1203 of the shaft 1202 adjacent the width-wise center of the distal cutting tip 1204. The syringe connector 1218 has a central axis $A_C$ that is axially offset and preferably obliquely angled by angle β relative to the longitudinal axis $A_L$ of the shaft. The angle β is preferably between 5°-90°, more preferably between 10°-45°, and even more preferably between 10-20°, and is adapted to orient a syringe 1320 connected at the syringe connector 1218 without interference with the handle 200, while also permitting operation of the plunger 1322 of the syringe 1320 in either a single handled or two-handed operation by the surgeon while holding the handle 1200 connected to the probe 1108.

Figure 26:
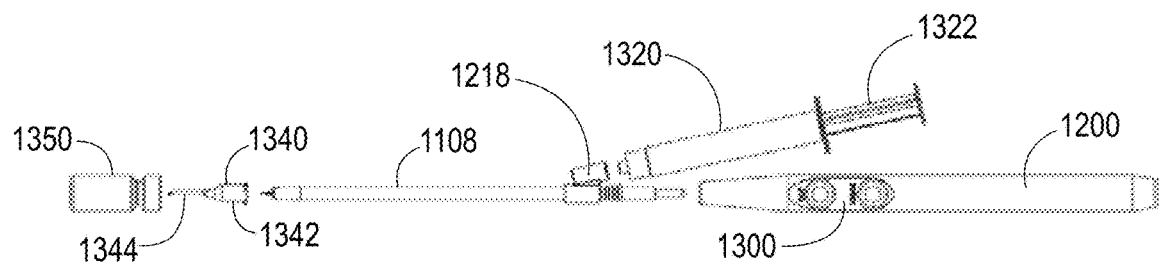
FIG. 26 is a side elevation of a cautery device system, with handle, needle adapter, and medical vial described herein.
Figure 27:
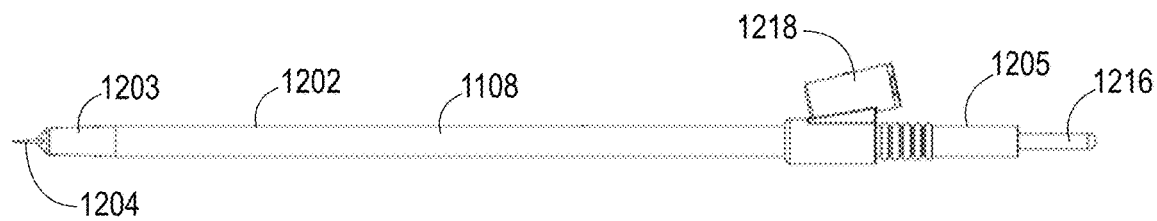
FIG. 27 is a side elevation view of the cautery device of the cautery device system.

Referring to FIG. 26, in one method of use, a syringe 1320 is coupled at syringe connector 1218, and a vial adapter 1340 is provided. The vial adapter 1340 includes a receiver 1342 that engages the tapered distal end 1203 of the shaft 1202, and a needle 1344 extending from in and fluid communication with the receiver 1342. The receiver 1342 can be a female Luer connector. The needle 1344 can have a sharp piercing tip. Alternatively, it can have other structure adapted to penetrate or otherwise open a septum or other closure of a medication vial. The receiver 1342 is positioned and secured on the tapered distal end portion 1203 of the shaft 1202. Importantly, when the distal end 1203 of the shaft 1202 is positioned in the receiver 1342, the metal tip 1204 does not bottom out within the receiver 1342. The dimensions and fit are designed in this manner. The needle 1344 is then inserted into the vial of medication 1350. Then the plunger 1322 of the syringe 1320 is drawn back to pull medication from the vial 1350, through the fluid lumen 1206, and up into the barrel of the syringe 1320. Then, the medical vial 1350 and vial adapter 1340 are removed from at the distal end 1203 of the shaft 1202 of the probe 1108 to re-expose the distal cutting tip 1204. The shaft 1202 of the probe 1108, attached to the handle 1200 either before or after the above-described process, is then operated in accord with one or more of the methods herein. As such, the preceding steps can be performed before, during, or after making an incision in the patient or before or after wanding the probe at a location in the patient. The probe can be employed for any appropriate purpose described herein. In addition, the described probe can be used in any other suitable electrocautery procedure.

The conductor of the electrode at the distal cutting tip 204, 1204 is relatively thick to provide provides stiffness, which allows the probe to be controlled like a wand without bending or breaking. The ability to wand the probe, as well as the power directed by the tip of the probe, enables an improvement in rhizotomy procedures, as discussed in more detail below. Further, in distinction from conventional electrocautery devices (such as of the type sold by Bovie Medical Corp.), the distal tip has a tapered and beveled surface leading to an edge that allows the distal tip 204, 1204 of an energized probe to function in place of a scalpel and make fine incisions.

Hereinafter, all references to handle 200, shaft 202, probe 108, or distal tip 204 or any other structure or features of the probe, shall be considered as referring separately and to the multiple embodiments of the probes described herein, as if the individual embodiments were separately set forth at each such instance. It is appreciated that the shaft 202 of the probe 108 and distal tip 204 therefor are intended to be portions of manual, handheld operated instruments, which are to be directly inserted through an incision. As such, they have a length preferably no longer than 300 mm (12 inches), more preferably less than 240 mm (9 inches), and more practically for most patients in a range not exceeding 100 mm to 160 mm (4 to 6 inches). This is in distinction from longer instruments that may be adapted for use with laparoscopic ports, but which would be unwieldy for the methods described herein.

Figure 4:
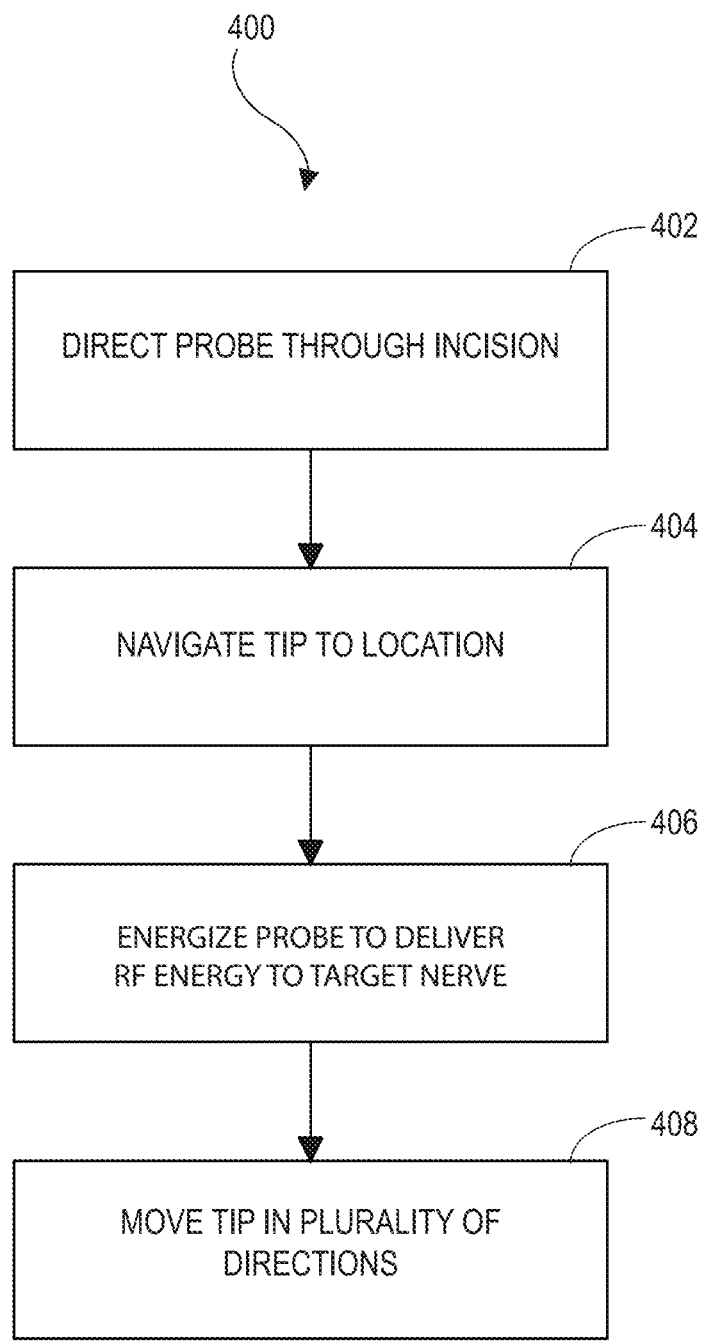
FIG. 4 is a flowchart depicting an example method in accord with the disclosure.

Turning now to FIG. 4, a flowchart depicts one exemplar method 400 for rhizotomy in accordance with this disclosure. The method 400 includes directing a probe through an incision in the body of a patient 402, navigating a distal tip of the probe onto a boney surface at or adjacent a target nerve 404, energizing the probe to deliver energy to the target nerve 406, and moving the distal tip of the probe in a plurality of directions to direct the energy at the target nerve 408. In embodiments, the probe is an electrocautery probe, and the energy is radiofrequency energy.

More particularly, the method 400 may be performed using the system 100 and the probe 108 of FIGS. 1-3B as follows. A physician may mark a location on the skin of a patient, e.g., using a metal localizer, and makes a small incision, e.g., 3 millimeters at the marked location. Using the handle 200, the physician may insert the distal tip 204 and shaft 202 of probe 108 through the incision into the body of the patient. The incision may be made by scalpel or other non-electrical sharp surgical instrument. Alternatively, the probe may be energized and operated to create the small, minimally invasive incision with the distal tip of the probe. The distal tip 204 of the probe is navigated under imaging to the target location within the patient by physician manipulation of the shaft 202 of the probe. Navigation is preferably conducted using fluoroscopy 110, including, e.g., intraoperative X-ray producing anterior-posterior, lateral, and oblique views.

A numbing agent is injected or otherwise applied at the skin and superficial tissues prior to making the incision.

The distal tip of the probe is optionally energized to deliver RF energy while the probe is placed through the incision and/or while the probe is navigated to the boney surface.

Once at the boney surface, preferably prior to ablating, cauterizing and transecting the nerve, the physician delivers numbing/desensitization and/or anti-inflammatory medicine to the target nerve. Other medicines may also be delivered. The medicines are preferably delivered through lumen 206 and out of aperture 214 to the target location. The numbing/desensitization and/or anti-inflammatory may include one or more of novocaine, bupivacaine, and methylprednisolone.

Then, the methods are carried out such that movement of the probe in the plurality of directions, in conjunction with the delivered energy, operate to ablate, cauterize and/or optimally transect the target nerve.

While the methods are preferable carried out with the application of RF energy to the target area while there is movement of the distal end of the probe in the plurality of directions over the boney surface of the bone in the target area, it is appreciated that alternative or additional forms of treatment and nerve modulation energy may be applied. By way of example only, the probe may alternatively or additionally be a laser probe for delivering laser energy to the target area, a mechanically abrasive probe for delivering abrasion over to the target area, a chemical delivery probe for delivering a chemical necrotic agent to the target area, a cryogenic cooling probe for causing necrosis of the target nerve at the target area, an ultrasonic energy delivery probe for delivering ultrasonic energy to the target area, a microwave energy delivery probe for delivering microwave energy to the target area, or other energy or stimulation delivery probe activatable for carrying out ablation and/or transection of the target nerve at the target area.

Figure 5:
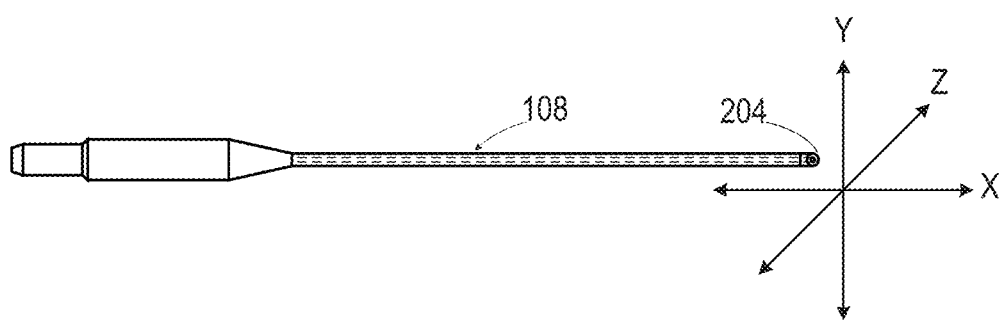
FIG. 5 illustrates wanding motion of a cautery probe, where the distal tip is able to move in any 3D direction.

The treatment energy is preferably applied for a time period in a range from approximately 3 seconds to approximately 10 seconds. Additionally, while the physician is energizing the distal tip 204 of probe 108, the physician moves the distal tip 204 in the several dimensions of movement, and preferably through the three dimensions of movement both along and above the boney surface. Turning to FIG. 5, the three dimensions are preferably in X, Y and Z planes along a boney surface where the nerve extends and adjacent the target nerve, as well as above the boney surface in the locations adjacent the target nerve. Movement above the boney surface is preferably up to 5 mm above the boney surface. Such multi-dimensional movement of the distal end of the probe in the area of the target nerve while the probe is energized ensures that the nerve is ablated, cauterized, and optimally transected such that it is permanently prevented from regenerating.

For example, the physician may move distal tip 204 laterally, medially, rostrally, caudally, and/or anteriorly, posteriorly, as well as on and off the bone adjacent the expected location at which the medical branch of the dorsal ramus nerve extends along the vertebra. The movement of distal tip 204 may include lateral-to-medial and/or medial-to-lateral movement, and/or rostral-to-caudal and/or caudal-to-rostral movement, and/or anterior-to-posterior and/or posterior-to-anterior movement along the bone and above the bone. Moving the distal tip both along the bone and above the bone may be important, as it has been recognized by applicant that the target sensory nerves at the treatment sites do not always extend flush with the bone surface and may unpredictably extend away from the boney surface and then return. Additionally, to steer the surface 208 of the distal tip 204 of the probe 108, the physician may twist/spin distal tip 204 around the longitudinal axis of shaft 204. It has been found that movement of the probe tip, as set forth herein, to extend through an area on and above a target location relative to the boney surface over which the target sensory nerve is expected to traverse has predictably reliable results in successful transection of the target sensory nerve. Depending on the nerves treated at a target location, the size of the wanded treatment area may be as small as 10 mm$^2$, up to and larger than 25 mm$^2$, up to and larger than 50 mm$^2$, up to and larger than 100 mm$^2$, up to and larger than 200 mm$^2$, up to and larger than 300 mm$^2$, up to and larger than 400 mm$^2$, up to and larger than 500 mm$^2$, and even up to 1000 mm$^2$ for various therapeutic treatment applications. Because the nerves can be small dimensions and extend in different routes on different patients, the relatively large wanded treatment areas increase the probability of successfully treating the target nerve. This is in contrast to prior RFA needle ablation treatments which are point treatments to a target that exists at an uncertain target location.

Additional burn regions to ablate, cauterize or transect other sensory nerves on the same or adjacent bones forming the joint can be performed. In most situations, the probe can be directed to the other sensory nerve regions without removing the distal tip of the probe from the incision. After sufficiently ablating, cauterizing or treating tissue, including transecting the nerve, at the target location with RF energy using probe 108, the physician can deactivate the probe, retract the instrument, apply pressure to the incision in case of any bleeding, and close the incision. Alternatively, after transecting the nerve, the probe can be used in its coagulation function to stop bleeding of tissues near the treated nerve, at the incision, or tissues therebetween.

For treatment of other areas, it may be preferred or necessary to treat a joint via an approach from multiple incisions. In a manner similar to the above, a first treatment location is accessed and one or more target nerves are treated at the first target location via wanding the probe tip along and above a boney surface to ablate and/or cauterize and optimally transect one or more nerves in a first wanded area. Then, the probe can be removed from the incision and delivered to a second treatment location, and one or more target nerves are treated at the second target location via wanding the probe tip along and above a boney surface thereat to ablate and/or cauterize and optimally transect one or more nerves in a second wanded area. The probe can be delivered to additional treatment locations, as necessary, to treat the joint.

The following describes specific treatments. For sake of clarity and brevity, treatments are described using an RF probe. It is within the scope of this disclosure that the treatments can similarly be performed using other types of treatment probes described herein and their corresponding energy, chemicals, or modalities to disrupts the function of the target nerve.

Cervical Spine Rhizotomy

More specifically, a rhizotomy procedure on the cervical spine 500 may be practiced as follows. With the use of medical imaging including intraoperative fluoroscopy, the appropriate cervical facet joint may be identified on anterior-posterior (AP), lateral, and oblique diagnostic imaging for purposes of localization and navigation. The patient may be prepped and draped in a standard sterile fashion. The patient may be positioned prone, and the back of the neck is sterilely prepped and draped. A diagnostic x-ray may be used for localization and navigation with AP, lateral, and oblique views. A surgical incision may be marked out directly above the affected facet joint, and local analgesic may be infiltrated under the skin near the surgical incision marking. A small incision is made (e.g., a 3 mm incision such as may be made using a #11 scalpel), and an electrocautery probe is advanced through the soft tissues targeting the lateral edge of the lateral mass 530 above and below the affected facet joints 532. The probe may be advanced through the soft tissues under medical imaging guidance. The probe may be docked on the boney surface in the middle of the lateral mass 530 below and above the facet joints 532 sequentially. Alternatively, without prior incision, the energized probe is percutaneously advanced at the marking site, and navigated under medical imaging guidance cutting through the soft tissues to target the lateral edge of the lateral mass 530 above and below the affected facet joints 532, and then docked on the boney surface in the middle of the lateral mass below and above the affected facet joint. In addition, one or more analgesic may be injected at the marking site prior to advancing the probe and continuously or intermittently while advancing the probe. The injection may occur while the probe is energized with sufficient RF energy at the distal tip to cut or coagulate adjacent tissue, or the electrosurgical generator may be operated to interrupt RF energy during analgesic injection.

The energized tip of the device may be wanded from the top of the lateral mass to the bottom of the lateral mass both above and below the affected facet joint along the lateral edge of the lateral mass essentially running from the bottom of the facet capsule of the lateral mass below the affected facet joint for denervation and rhizotomy of the affected nerves along the lateral third of the lateral mass from the top of the lateral mass to the bottom. This wanding motion with the probe in the active mode may rhizotomize and destroy the nerves innervating the facet joint that run along the lateral border of the lateral mass both below and above the affected facet joint. This procedure may be performed at the lateral mass both above and below the affected facet joint to denervate the facet joint using the wand. The physician is able to control the movement of the tip of the probe and allow for a wider burn field to incorporate all the possible locations of the nerve innervating the facet joint to allow a denervation of that facet joint. For multiple facet joints, the treatment is repeated again coagulating along the lateral third of the lateral mass both above and below the affected facet joints to the edge of the lateral mass laterally where it falls off anteriorly to ensure adequate coagulation of all potential locations of the nerves innervating that painful facet joint. The procedure preferably requires 3 to 10 seconds per lateral mass treated.

Figure 6:
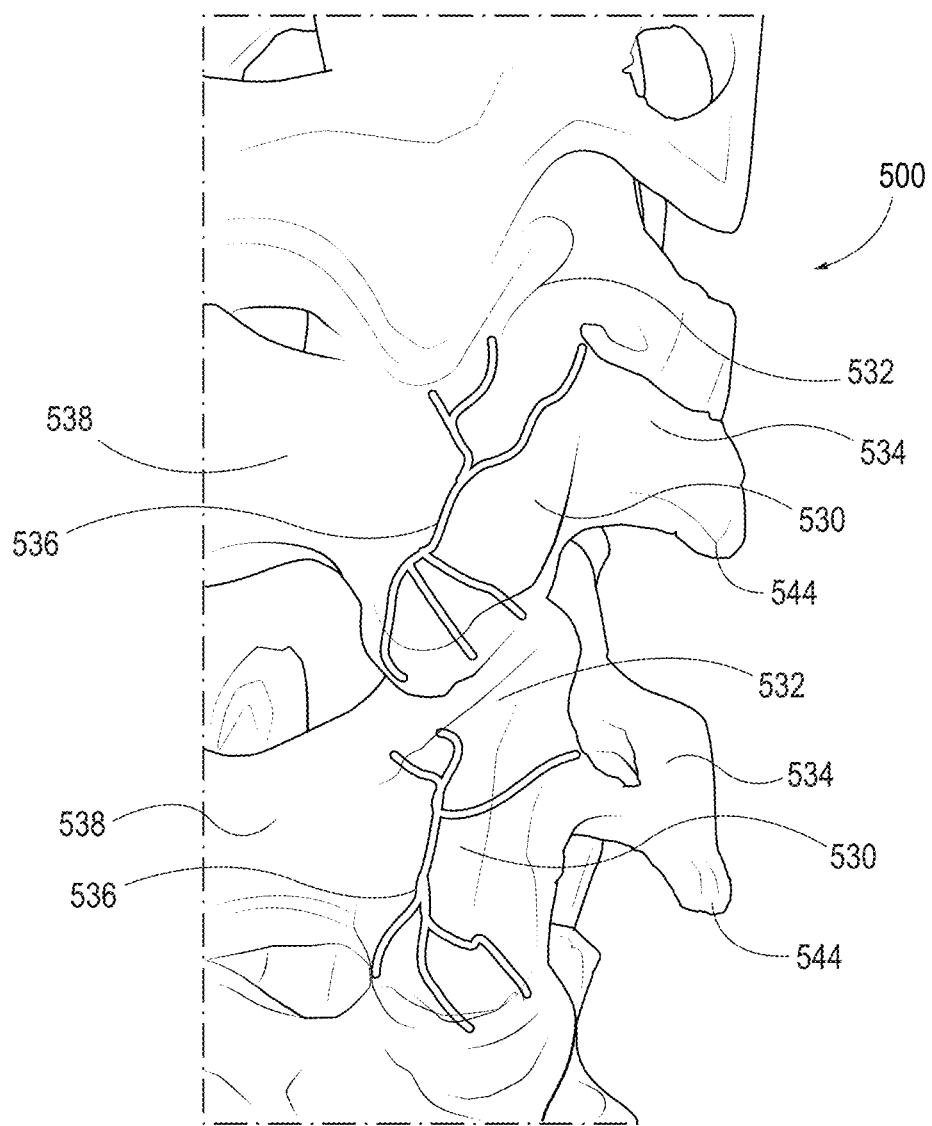
FIGS. 6 to 10 illustrate distinctions between a conventional radio frequency ablation (RFA) and wanded cautery rhizotomy procedure as described herein using a model of a cervical spine.
Figure 7:
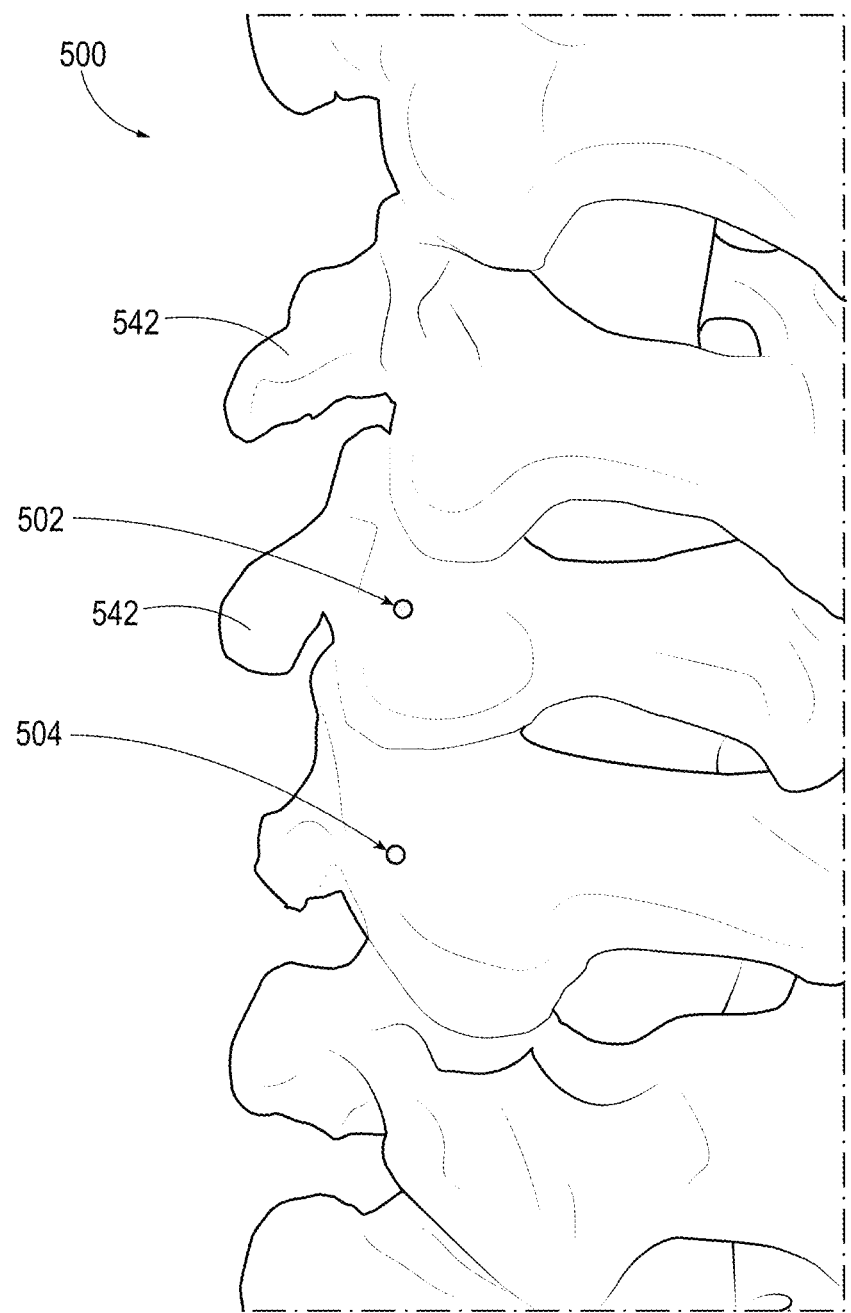

FIGS. 6 to 10 illustrate distinctions between a prior radio frequency ablation (RFA) with a needle and the higher energy radio frequency cautery cautery probe and procedure described herein, referred to herein as a wanded cautery rhizotomy procedure, using a model of a cervical spine. FIGS. 6 and 7 illustrate a portion of the cervical spine 500 with vertebrae 534 and targeted nerves 536. Each vertebra 534 includes lamina 538 that connects the spinous process 542 and the transverse process 544. Facet joints 532 function as a hinge between adjoining vertebrae 534, enabling some spine movement such as bending and twisting. Each vertebra 534 has a superior articular facet that faces upward and an inferior articular facet that faces downward. The superior articular facet from one vertebra forms a facet joint with the inferior articular facet from another vertebra. The medial branch of the dorsal ramus is the target sensory nerve that extends from the facet joint 532 at the cervical spine. As such, rhizotomies may target the medial branch of the dorsal ramus.

In known radio frequency ablation (RFA), a very flexible needle is utilized to perform rhizotomies. A stylus within the needle may be used to insert the needle to a pinpoint target. Once inserted, the flexible needle remains stationary until it is removed. After removing the stylus, the energy may be applied at the pinpoint target to ablate the tissue around the needle point. However, the location of targeted nerves can vary from patient-to-patient, making it difficult to conclude with certainty that the pinpoint target includes the nerves to be ablated. Another problem with known rhizotomy procedures is that the needle needs to be removed and reinserted into the patient to a different pinpoint target to target a different nerve. Furthermore, a facet joint may be innervated by both a medial branch of a dorsal ramus descending from a superior spinal nerve and a medial branch of a dorsal ramus ascending from an inferior spinal nerve. Both of these nerves may be targeted for the rhizotomy procedure. However, as known rhizotomy procedures use a flexible needle, the needle may need to be placed two separate times into position for both of these pin-point targets. FIG. 7 illustrates a portion of the cervical spine at which small RFA pin-point burn regions 502, 504 are made using conventional RFA rhizotomies in an attempt to disrupt the medial branch of the dorsal ramus.

Figure 8:
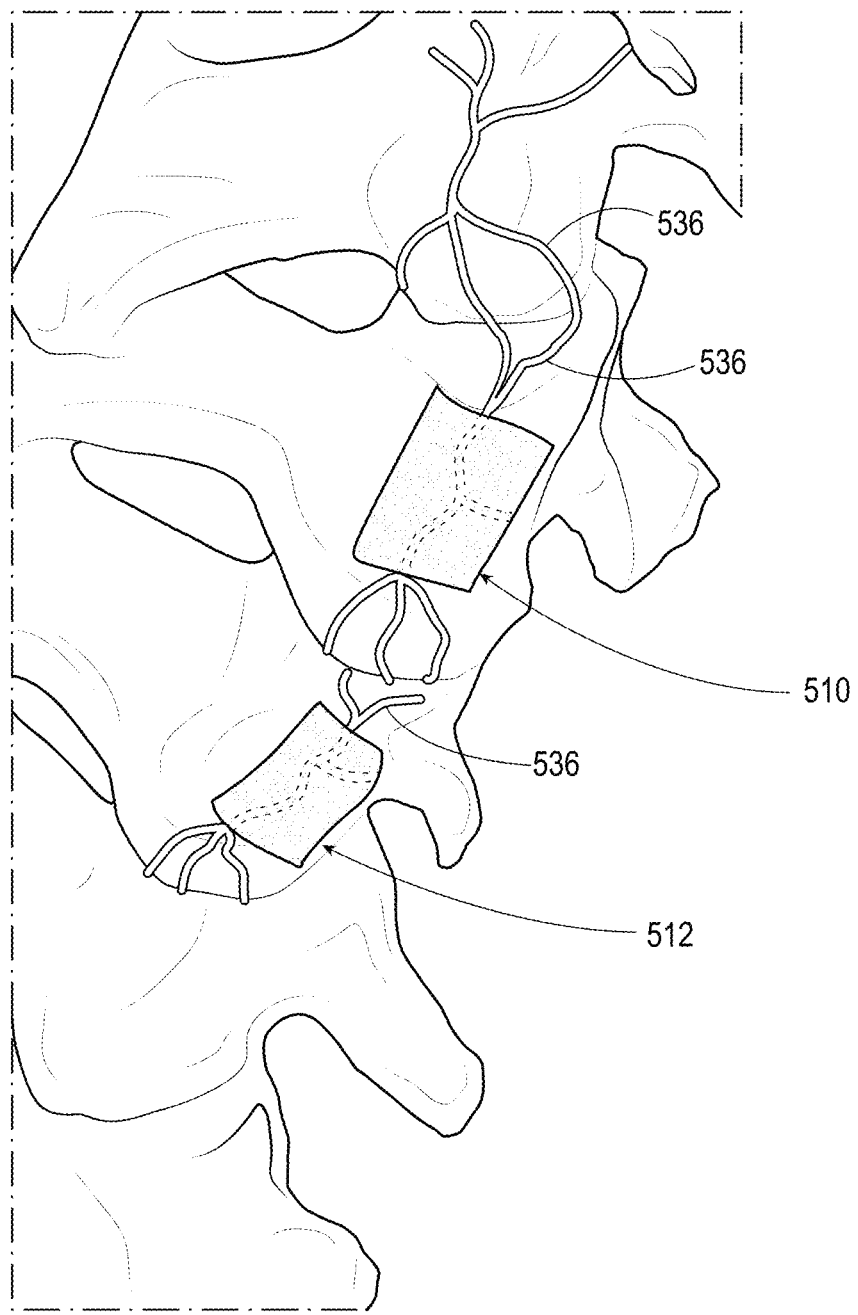

In contrast, as illustrated in FIG. 8, the wanded cautery rhizotomy procedure can provide large burn areas 510, 512 where the medial branch of the dorsal ramus 536 is expected to be located to permanently interrupt the sensory nerve signals from passing at those locations. It is noted that the illustration shows the wanded area over a central branched portion of the nerve. The wanded area can be over an extension of a single extension of the nerve or a branched portion. and the large size of the wanded area is intended to increase the probability and confidence level that the nerve will extend within the wanded area and be destroyed by the treatment. The same approach is preferably applied for treatment locations for target nerves of all joints. Further, the electrocautery probe may be located within a first region, energized and wanded to create a first burn area 510 covering the first regions, turned off, and then moved to a second region without being fully retracted, and then turned back on to create a second burn area 512 covering the second region. The process can be repeated as necessary for other regions without removing the distal end of the probe from the patient or requiring a second probe.

Figure 9:
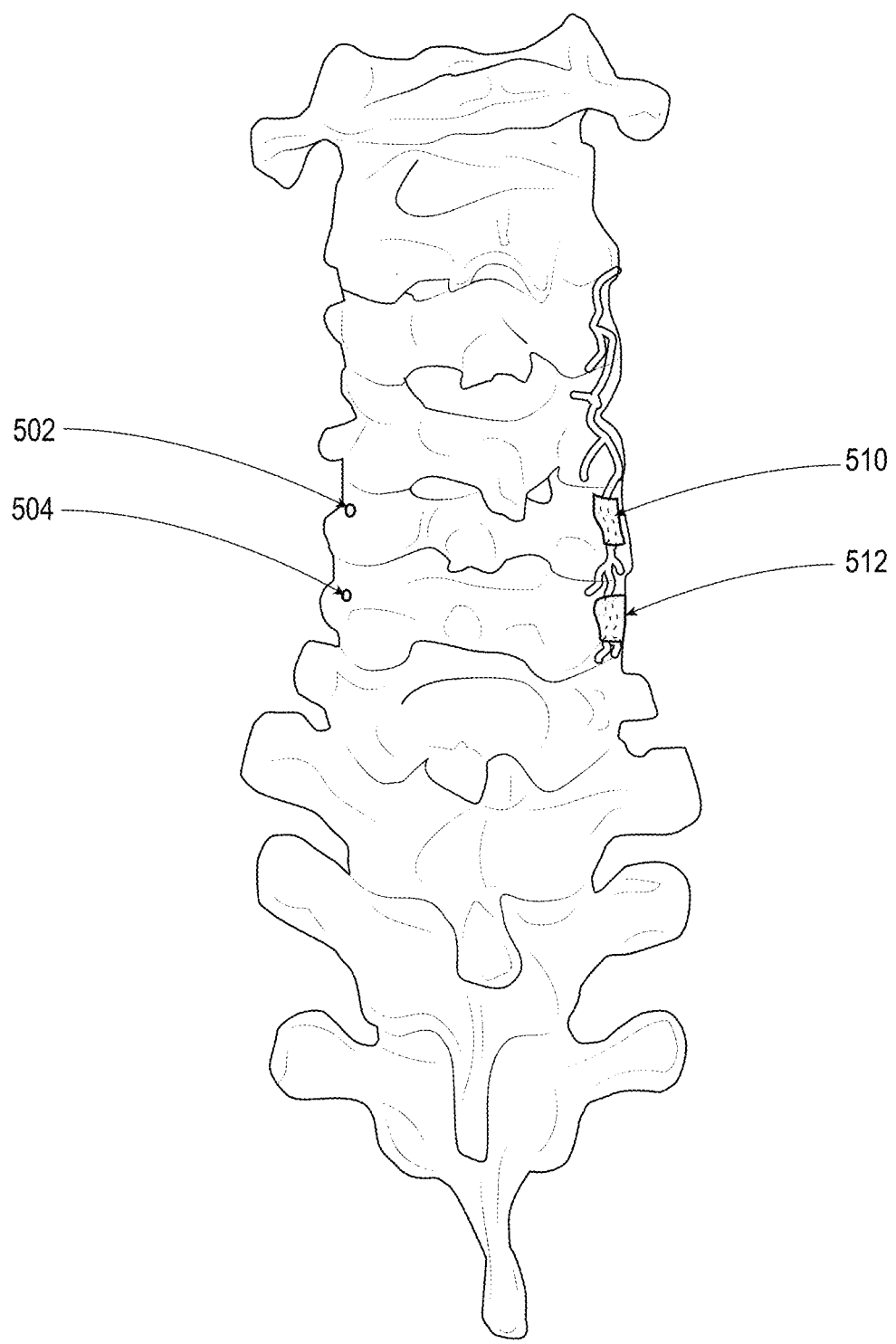
Figure 10:
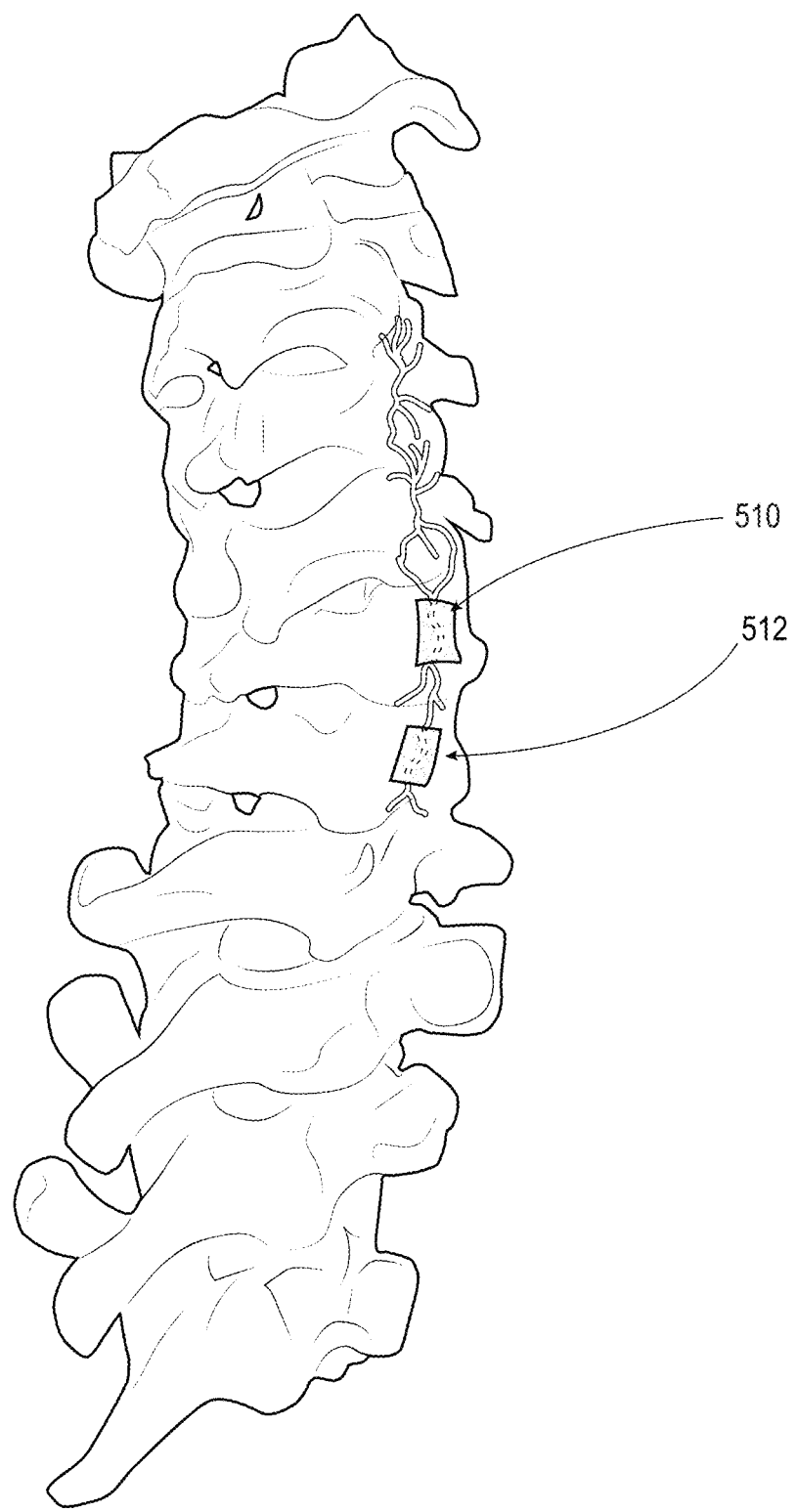

FIG. 9 illustrates a larger portion of the spine 500, and further provides a comparison of small pin-point RFA burn regions 502, 504 on the left side and wanded cautery rhizotomy burn regions 510, 512 on the right side. The size of the wanded cautery rhizotomy burn regions 510, 512 are much larger than the RFA burn areas 502, 504 and will ablate the target tissue with more certainty than the pin-point size areas created by the small, flexible RFA needles. Additionally, the imaging and wanding process required to identify the location of and create one wanded cautery rhizotomy burn region and then to move, identify the location of, and create another wanded cautery rhizotomy burn region is simpler than inserting and then reinserting the flexible RFA needle. Wanded burn areas 510, 512 may be created through a single incision in the skin, whereas RFA burn areas are created through separate insertions of an RFA needle. FIG. 10 illustrates additional views of the cervical spine with the larger ablated/cauterized regions 510, 512 on the right side. The targeted nerve typically extends within the wanded cautery rhizotomy burn regions. The increased size and power output of the electrocautery probe described herein can facilitate improved clinical outcomes by allowing the physician to move the distal tip of the probe in vivo adjacent the approximated location of the target nerve, which increases the likelihood the nerve will be efficaciously affected, cauterized and optimally transected, by the RF energy delivered by the probe. Additionally, the increased size and power output of the probe delivers a larger field or zone of affected tissue when the probe is energized.

Lumbar Spinal Rhizotomy

A lumbar spine rhizotomy procedure according to the present subject matter may be termed a lumbar wanded cautery rhizotomy procedure. A thoracic spine rhizotomy procedure according to the present subject matter may be termed a thoracic plasma rhizotomy procedure. An examplar lumbar wanded cautery rhizotomy procedure for lumbar facet joints is now described, with it being understood that the thoracic and lumbar techniques are substantially the same.

Using medical imaging intraoperatively, the patient is positioned prone on the operating table. The patient's back is sterilely prepped and draped over the affected facet joints.

Next, using AP, lateral, and oblique fluoroscopic x-ray imaging, the standard location of the nerve innervating the facet joint is identified. A small 3 mm skin incision may be made with a scalpel over the affected facet joint. The electrocautery probe may be advanced through the incision and soft tissues under diagnostic imaging for localization and navigation. The probe may be advanced to the top border of the transverse process where it meets with the superior articular process at the transverse process both above the affected facet joint and below the affected facet joint. An initial target for docking the probe is the bone posterior to the transverse process where the transverse process meets the pedicle and superior articular process for each facet joint treated. Fluoroscopic guidance is used for navigation. Once the tip of the probe is in contact with the dorsal cortical bone of the transverse superior articular process junction, the probe is activated and coagulation of the soft tissues begins including the innervating medial branch of the dorsal ramus. The medial branch of the dorsal ramus are the nerves that innervate the facet joints in the lumbar spine and transmit pain signals from the painful joints to consciousness. These nerves run along the dorsal cortex of the transverse process emanating from the neuroforamen above and traveling along the surface of the bone within the soft tissues at the junction of the proximal one third of the transverse process and superior articular process, and pars interarticularis. The wanded cautery rhizotomy procedure is carried out in a field in three dimensions that includes the area along and above the base of the superior articular process lateral along the superior margin of the transverse process to the junction of the first proximal third of the transverse process to the middle third of the transverse process. The probe is energized and moved rostrally and caudally moved to the bottom of the transverse process in the same location to form another burn field. Once the coagulation of the area of the nerve innervating the facet joint is performed superiorly, the probe is moved to the inferior nerve location along the back of the transverse process and superior facet at the level below the affected facet joint. For each facet joint treated, the field is treated with wanded cautery rhizotomy above and below that facet joint in the same location at the junction of the transverse process and superior articular process and pars interarticularis. Once completed, the probe is removed and the incision is closed.

The above-described method and any method described herein can be modified in accord with the teachings herein. That said, procedures for making incisions and applying medicines can be modified accordingly.

Figure 11:
FIGS. 11 to 16 illustrate distinctions between a conventional radio frequency ablation (RFA) and a wanded cautery rhizotomy procedure as described herein using a model of a lumbar spine.
Figure 12:
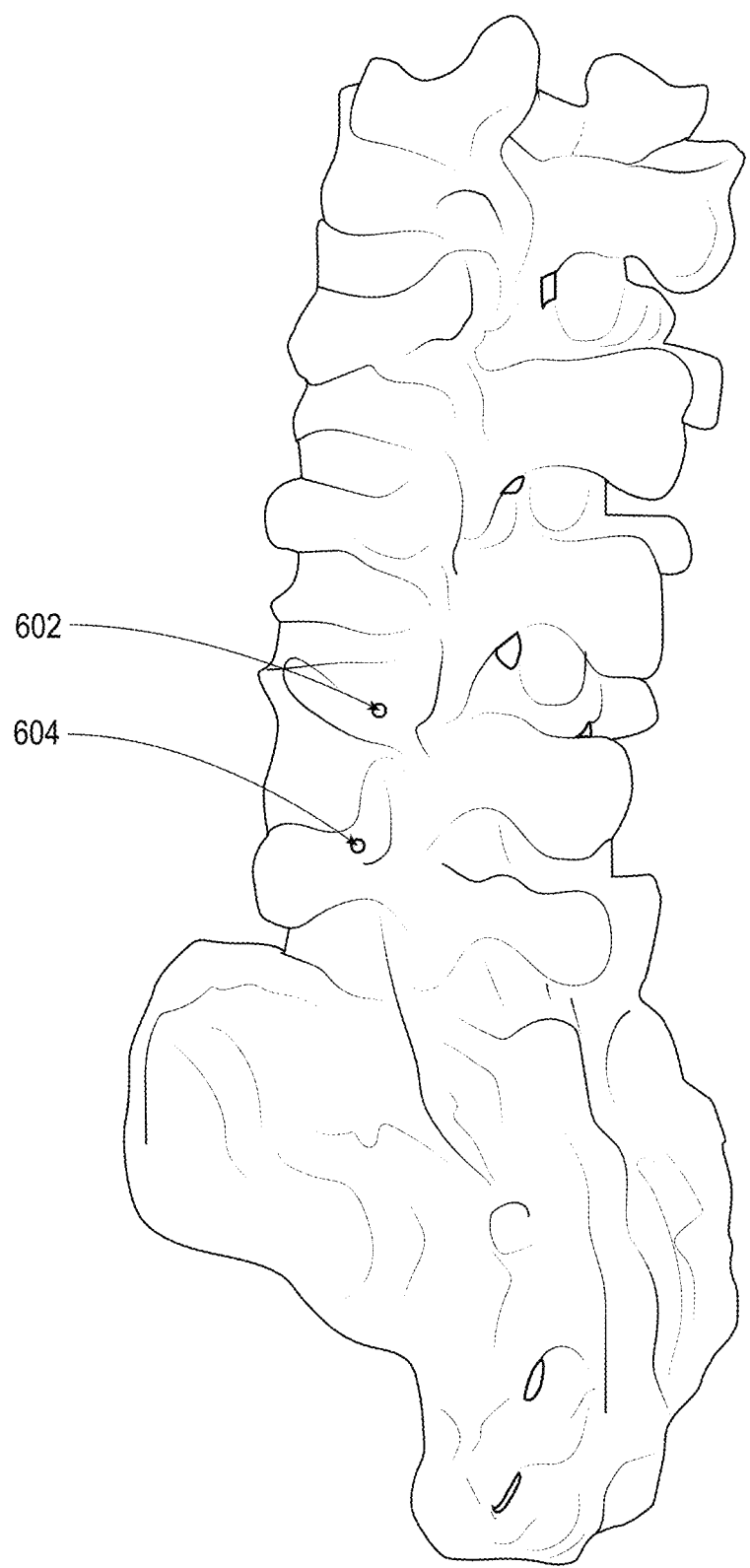
Figure 13:
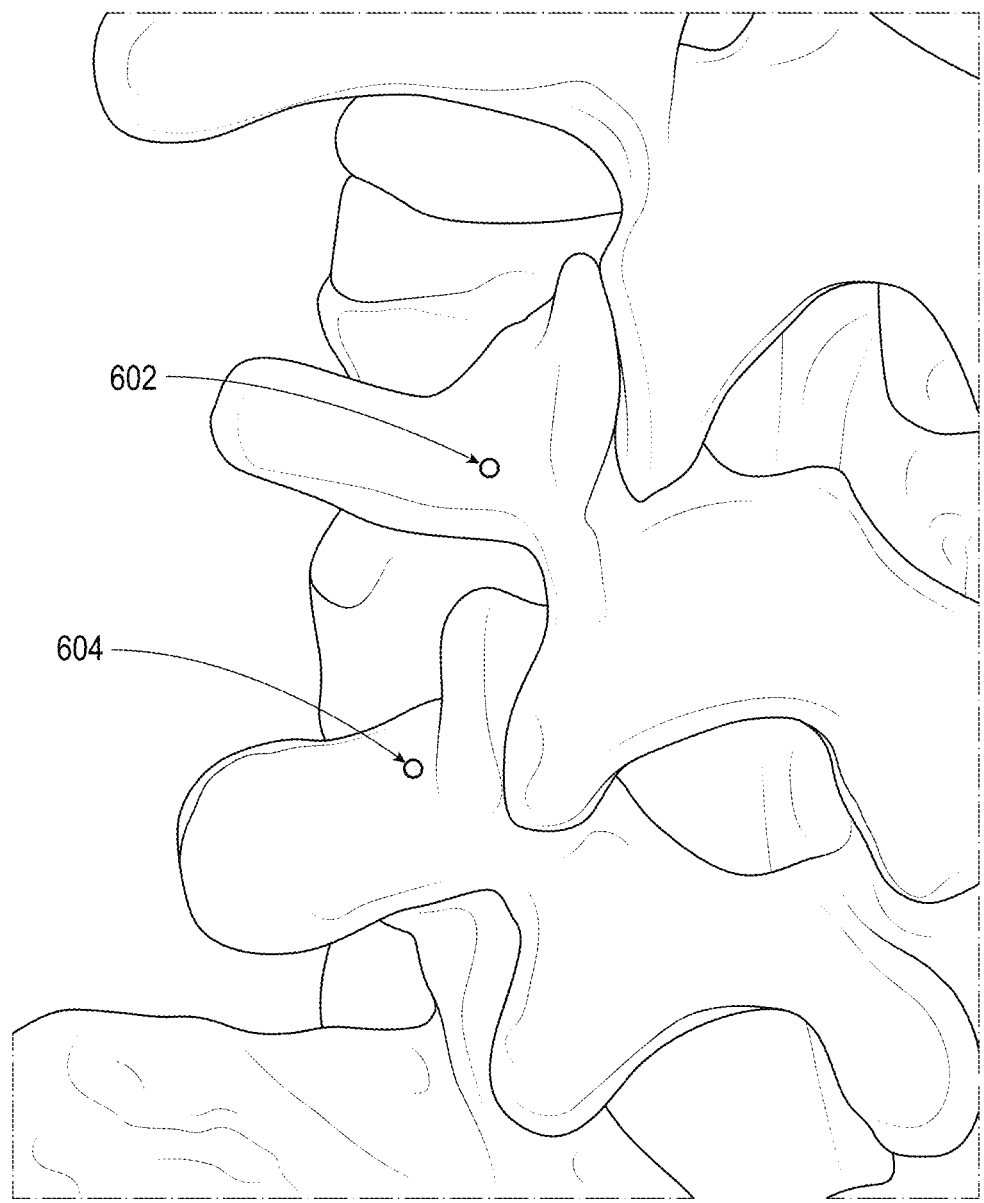
Figure 14:
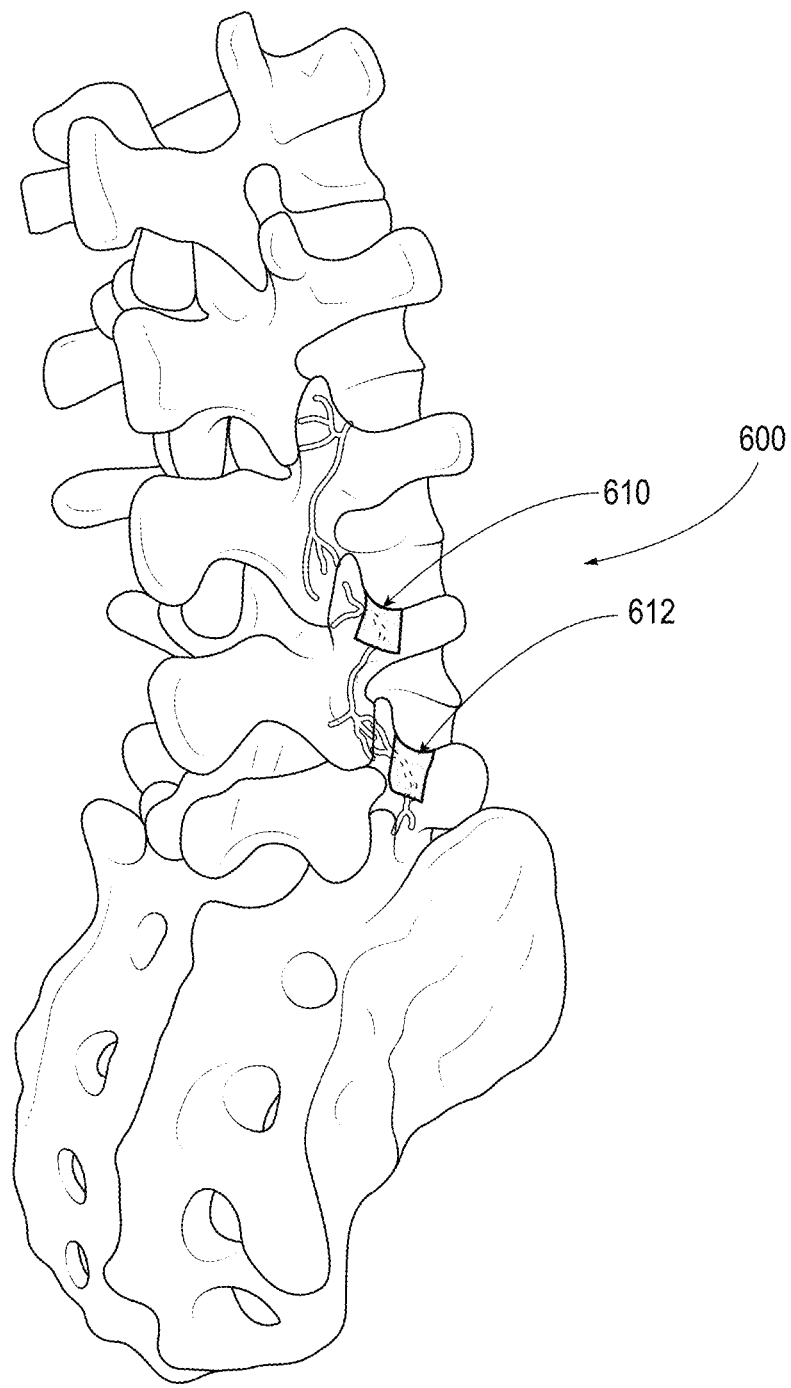
Figure 15:
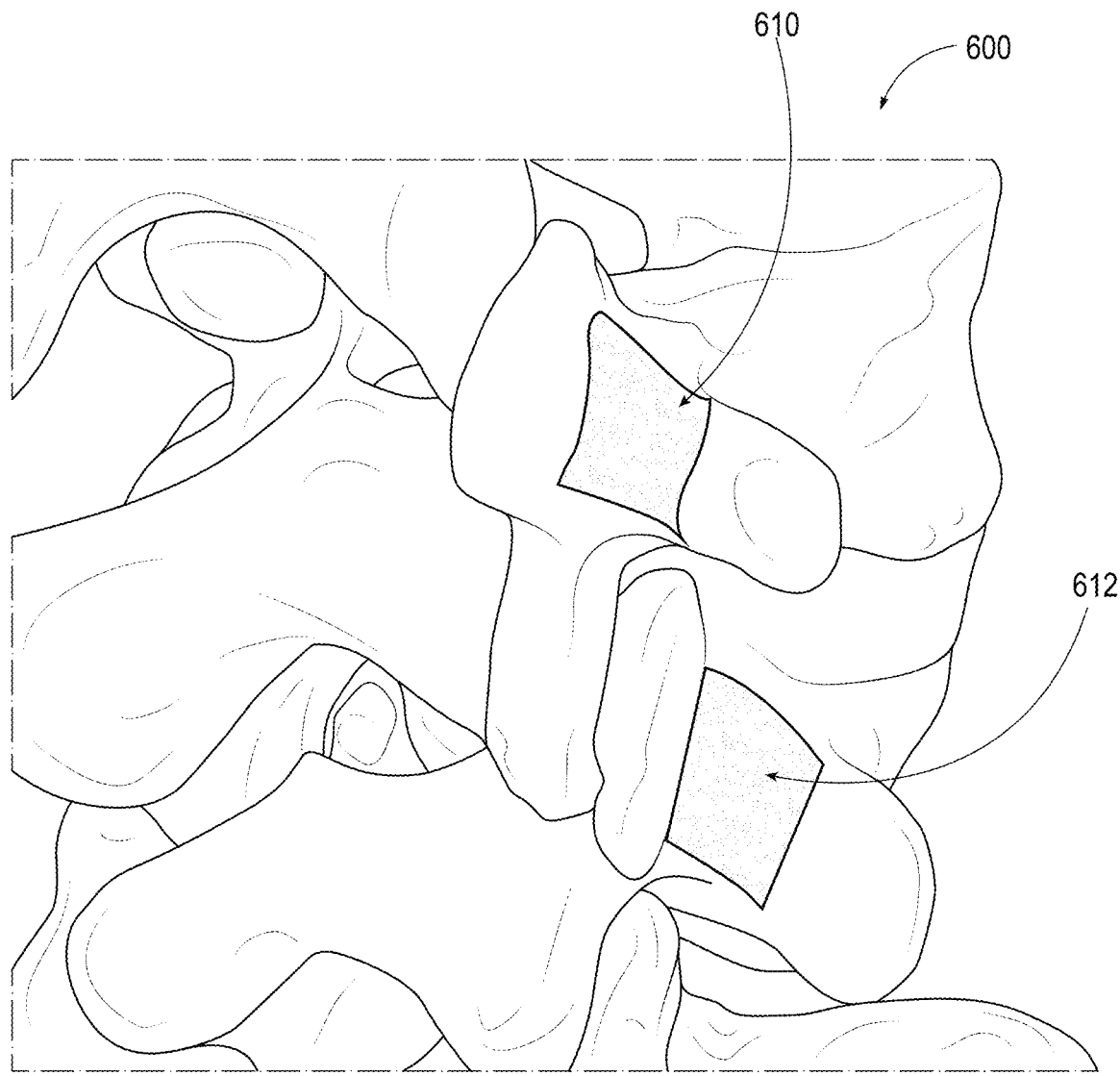
Figure 16:
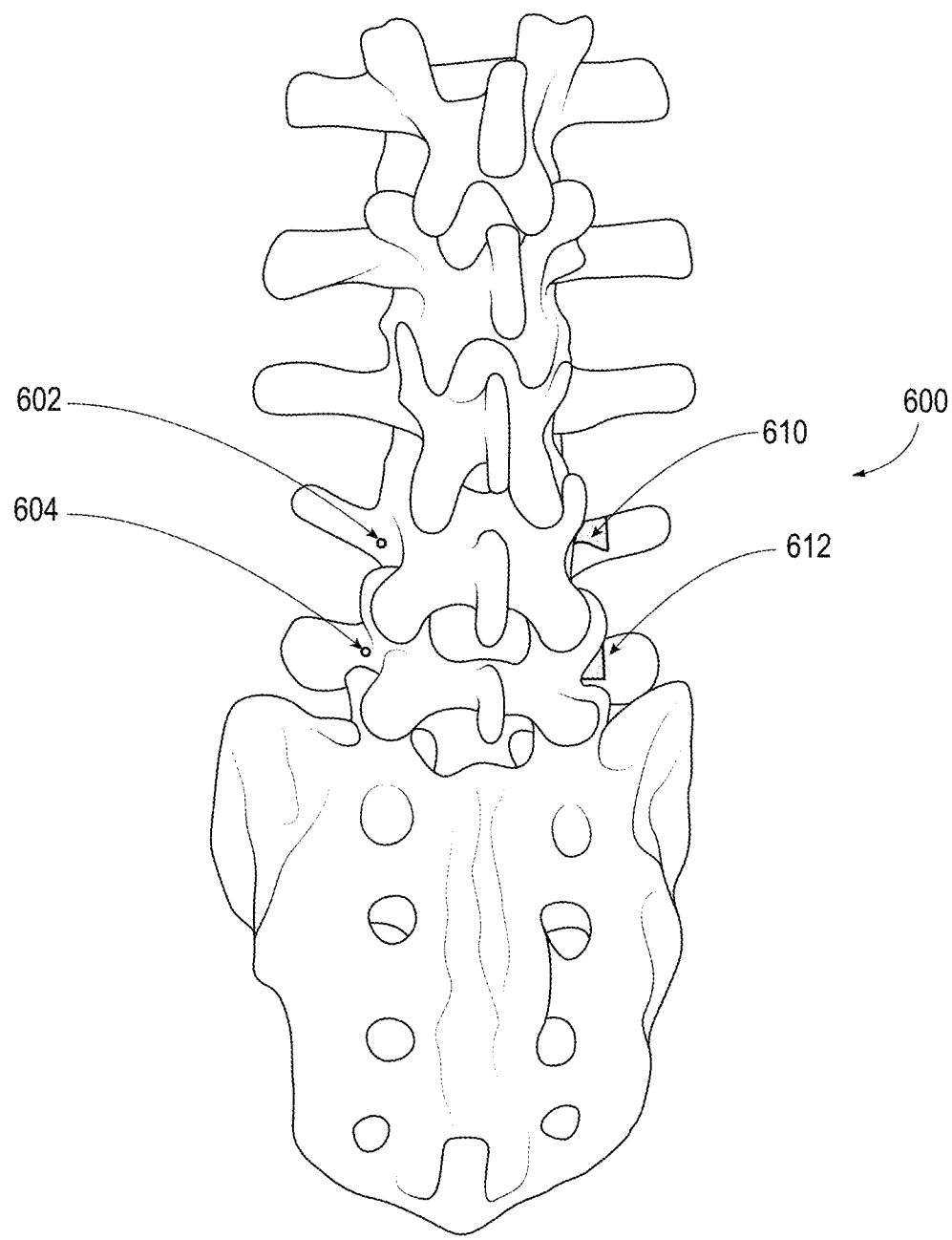

FIGS. 11 through 16 illustrate distinctions between a radio frequency ablation (RFA) and wanded cautery rhizotomy procedure using a model of a lumbar spine. FIG. 11 illustrates a portion of the lumbar spine and targeted nerves. FIGS. 12 and 13 illustrate a portion of the lumbar spine and small pin-point ablation regions 602, 604 provided by RFA. A stylus within the flexible needle used in known RFA rhizotomies may be used to insert the needle to a pinpoint target where the needle remains until it is extracted. The stylus may be removed and the energy is applied to ablate one of the RFA pinpoint targets. The needle may be removed and reinserted to ablate another RFA pinpoint target. FIGS. 14 and 15 illustrate a portion of the lumbar spine 600 and larger cauterized regions 610, 612 provided by the wanded cautery rhizotomy procedure. FIG. 16 illustrates a larger portion of the lumbar spine 600, with small pin-point RFA burn regions 602, 604 on the left side and larger wanded cautery rhizotomy burn regions 610, 612 on the right side. The size of the wanded cautery rhizotomy burn regions 610, 612 are much larger than the RFA burn regions 602, 604 and will ablate the target tissue with more certainty than the flexible RFA needles. The targeted tissue, comprising sensory nerves, typically passes along the portion of the vertebra within the wanded cautery rhizotomy burn regions. The increased size and power output of the electrocautery probe can facilitate improved clinical outcomes by allowing the physician to move the distal tip of the probe in vivo adjacent the approximated location of the target nerve, which increases the likelihood the nerve will be efficaciously affected by the RF energy delivered by the probe. Additionally, the increased size and power output of the electrocautery probe delivers a larger field or zone of affected tissue when the probe is energized. The probe may be wanded to create one wanded cautery rhizotomy burn region and then moved to create another wanded burn region; such procedure is simpler than inserting and then reinserting the flexible RFA needle.

The devices and techniques described herein can also be used to successfully treat chronic pain caused from the activity of sensory nerves at other joints in the human body. By way of example, the techniques can be used to pain at the shoulder joint, at the sacroiliac joint, at the hip joint, at the knee joint, at the ankle joint, and at the wrist joint.

Sacroiliac Joint Rhizotomy

Figure 17:
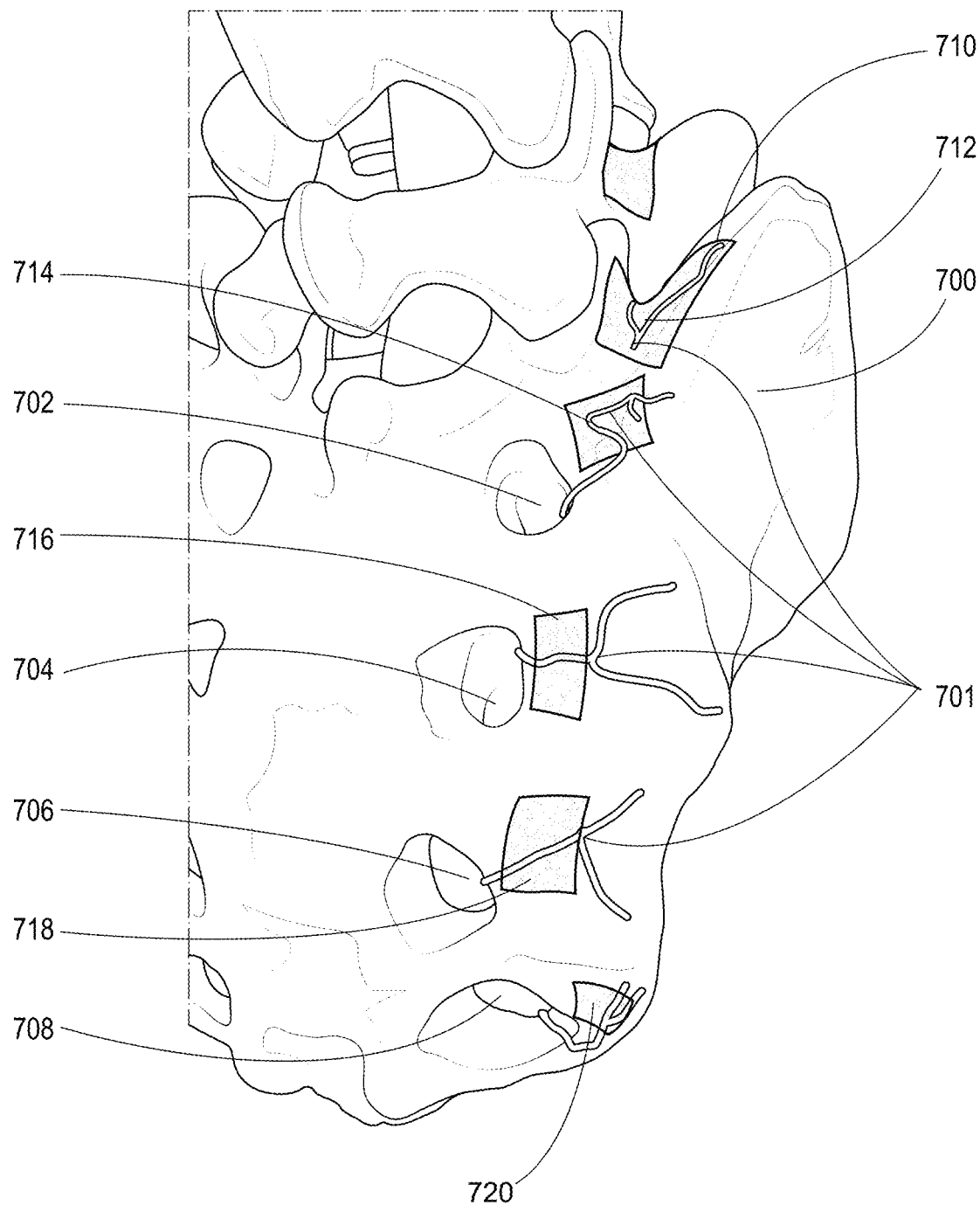
FIG. 17 illustrates target anatomy and the areas of treatment for a wanded cautery rhizotomy procedure on a sacroiliac joint.

Turning to FIG. 17, pain at the sacroiliac joint 700 can be treated by targeting for cauterization and transection using techniques described herein, the sensory nerves that innervate the sacroiliac joint immediately outside the sacroiliac joint. The procedure is carried out to target at least one of, and preferably all of, the following nerves: the dorsal ramus branch nerves 701 extending between the S1, S2, S3 and S4 posterior foramen 702, 704, 706, 708, respectively, and the sacroiliac joint 700 they innervate; and the L5 dorsal ramus nerve 710 by cauterizing respective wanded burn regions 712, 714, 716, 718 and 720.

Shoulder Joint Rhizotomy

Figure 18:
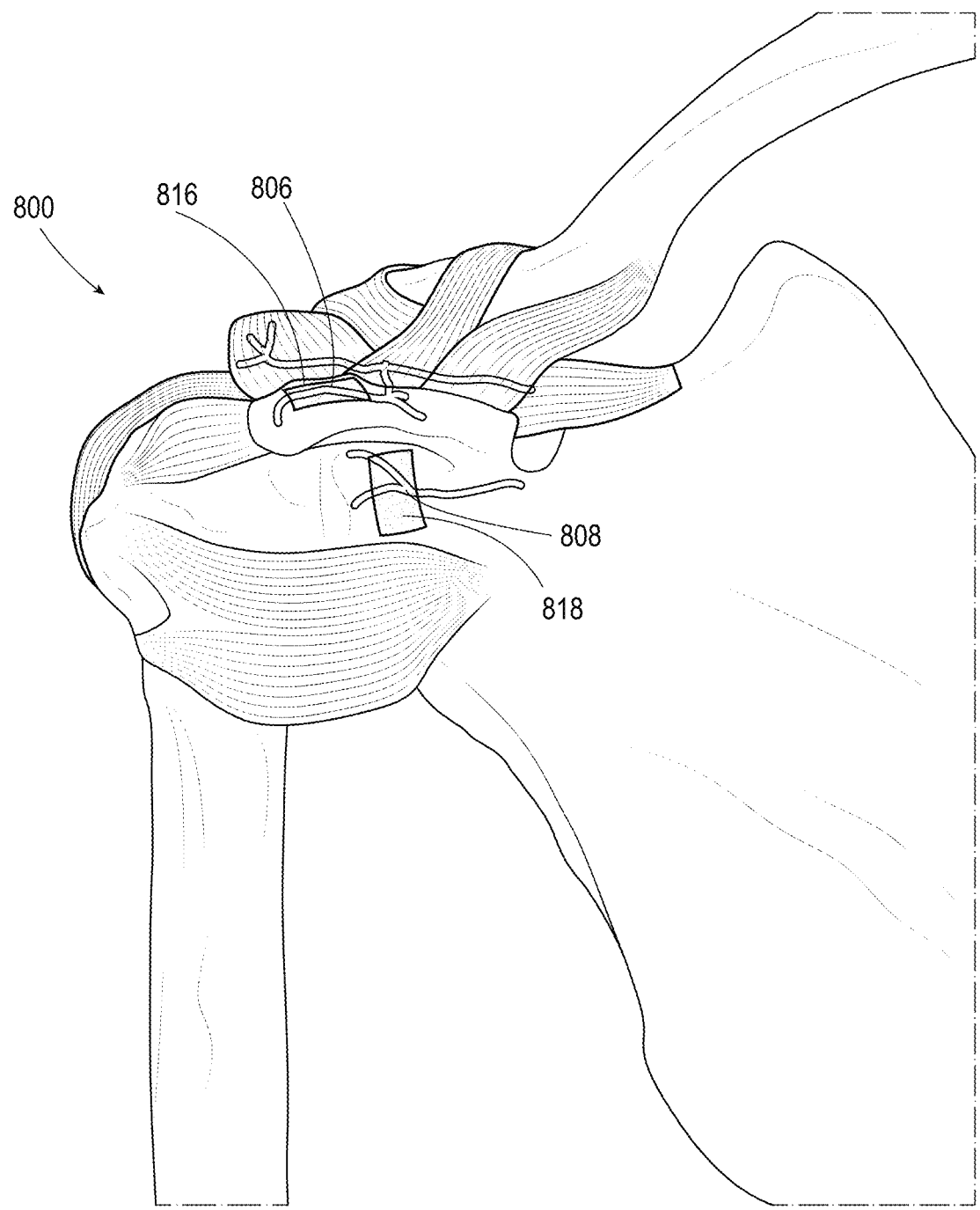
FIGS. 18 to 20 illustrate target anatomy and the areas of treatment for a wanded cautery rhizotomy procedure on a shoulder joint, with FIG. 18 illustrating the right anterior shoulder joint, FIG. 19 illustrating the lateral shoulder joint, and FIG. 20 illustrating the right posterior shoulder joint.
Figure 19:
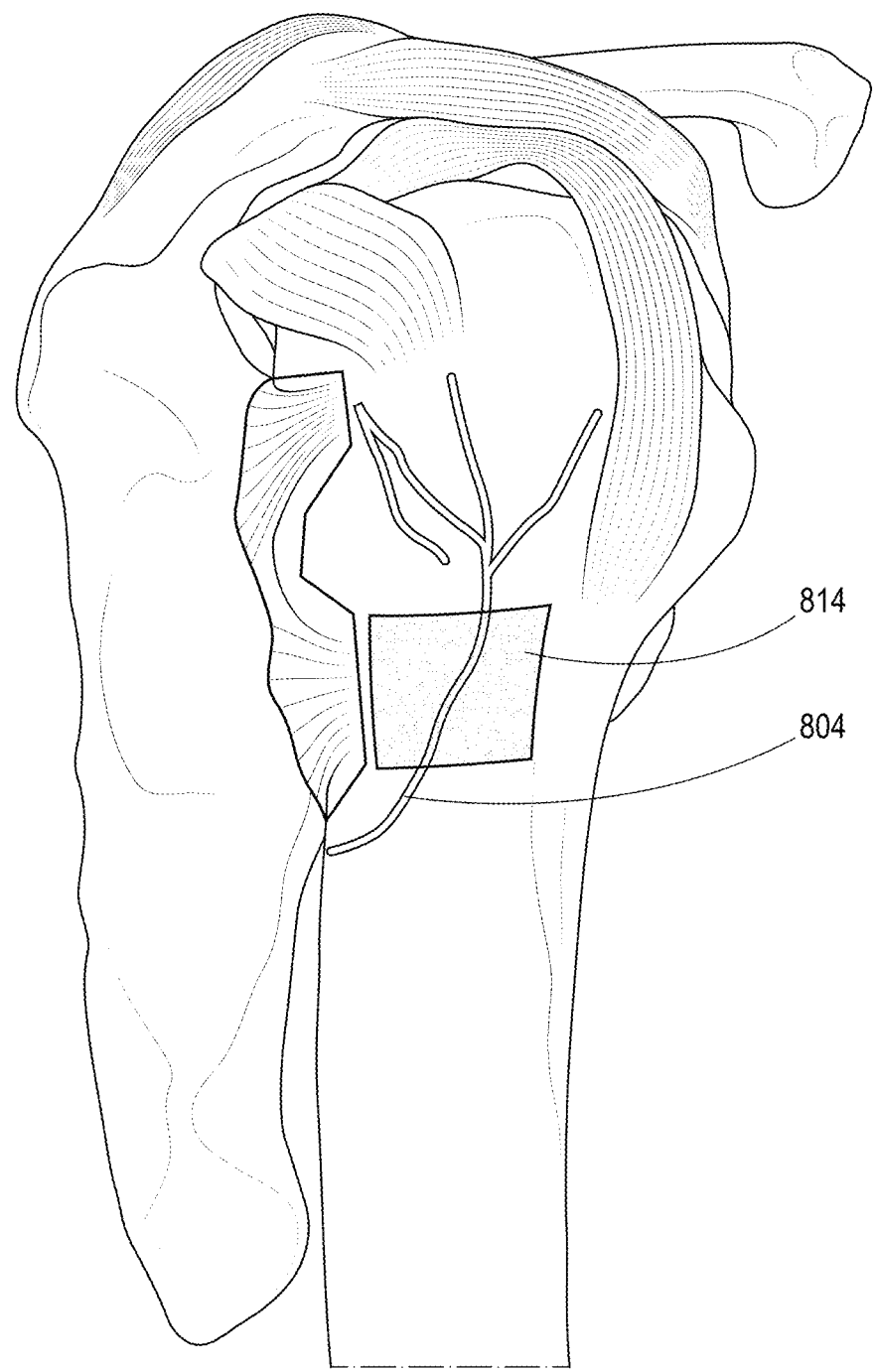
Figure 20:
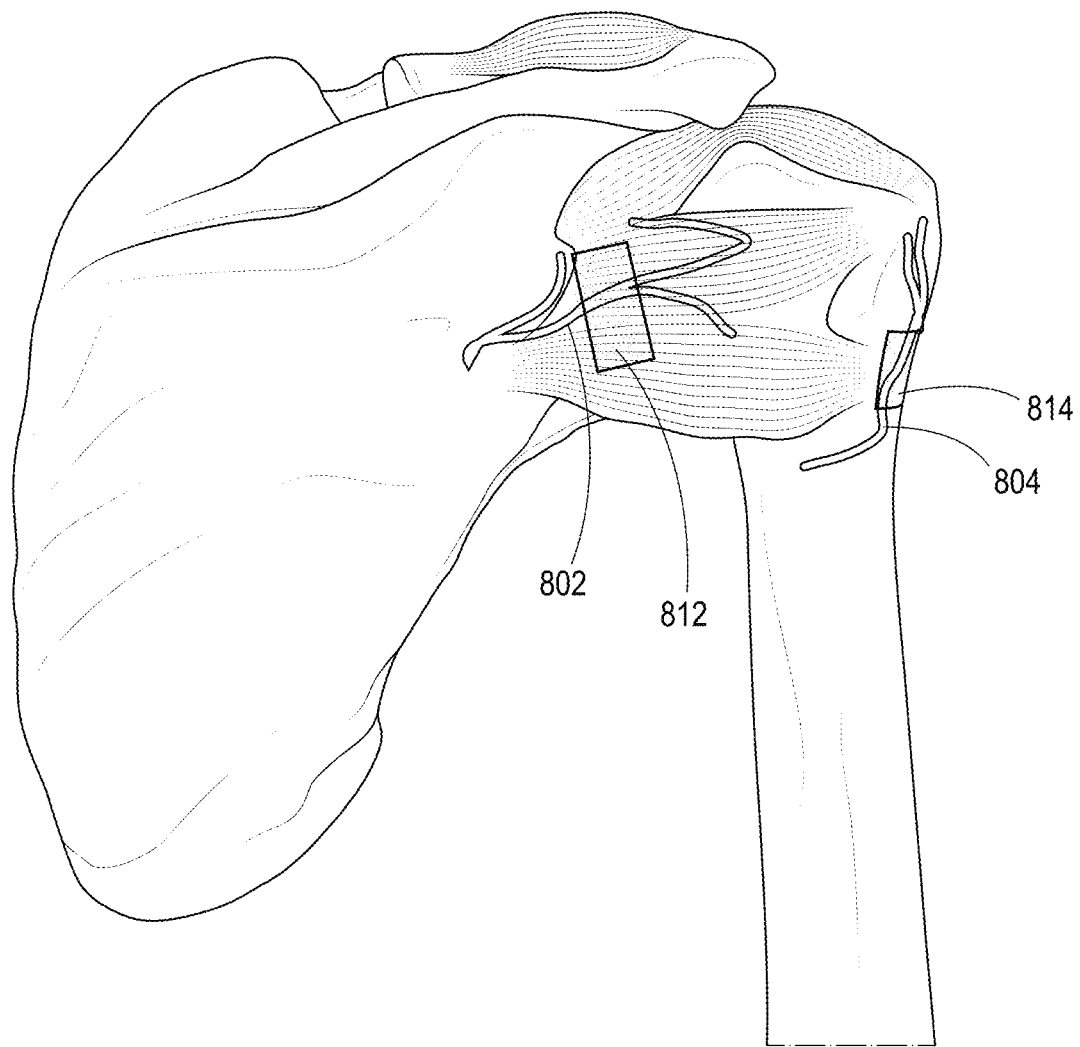

Referring to FIGS. 18 through 20, pain at the shoulder joint 800 can be treated by targeting for cauterization and transection with techniques described herein, the sensory nerves that innervate the shoulder joint and which reside immediately outside the joint. The procedure is carried out to target at least one of, and preferably all of, the following sensory nerves: an articular branch of the suprascapular nerve 802, an articular branch of the axillary nerve 804, an articular branch of the lateral pectoral nerve 806, and an articular branch of the subscapular nerve 808. In an embodiment, the nerves are targeted as follows. The articular branches of the suprascapular nerve 802 cauterized in a burn region 812 along the posterior neck of the scapula at the base of the glenoid moving in a superior-to-inferior direction or vice versa. The area of treatment is lateral to the spinoglenoid notch. The location of treatment of the articular branches are referred to the medial and lateral subacromial branches and the posterior glenohumeral branch. The articular branches of the axillary nerve 804 are cauterized in a burn region 814 ascending along the lateral border of the head of the humerus between the greater tuberosity, the lateral metaphysis, and the surgical neck of the humerus. The articular branches of the lateral pectoral nerve 806 are cauterized in a burn region 816 along an anterior surface of the coracoid process. The articular branches of the subscapular nerve 808 are cauterized in a burn region 818 along an anterior superior scapular neck proximal to the joint. While it is stated that the articular branches are cauterized in the respective burn regions, it is within the scope herein to cauterize and transect the respective nerve prior to branching such that only a single branch of the respective nerve is required to be ablated and transected to achieve the intended therapeutic result.

Hip Joint Rhizotomy

Figure 21:
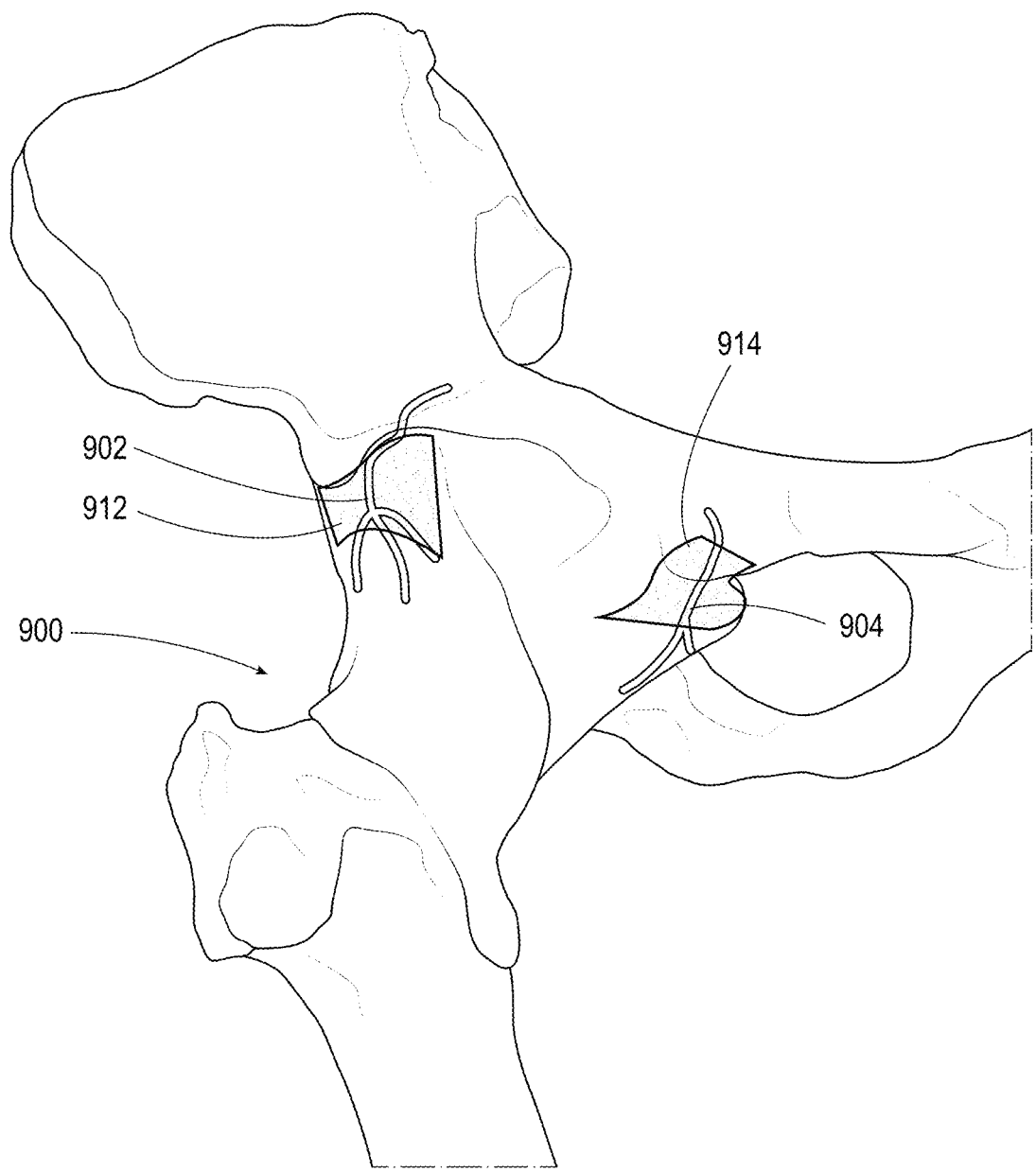
FIGS. 21 and 22 illustrate target anatomy and the areas of treatment for a wanded cautery rhizotomy procedure on a hip joint, with FIG. 21 illustrating the right anterior hip joint, and FIG. 22 illustrating the right posterior hip joint.
Figure 22:
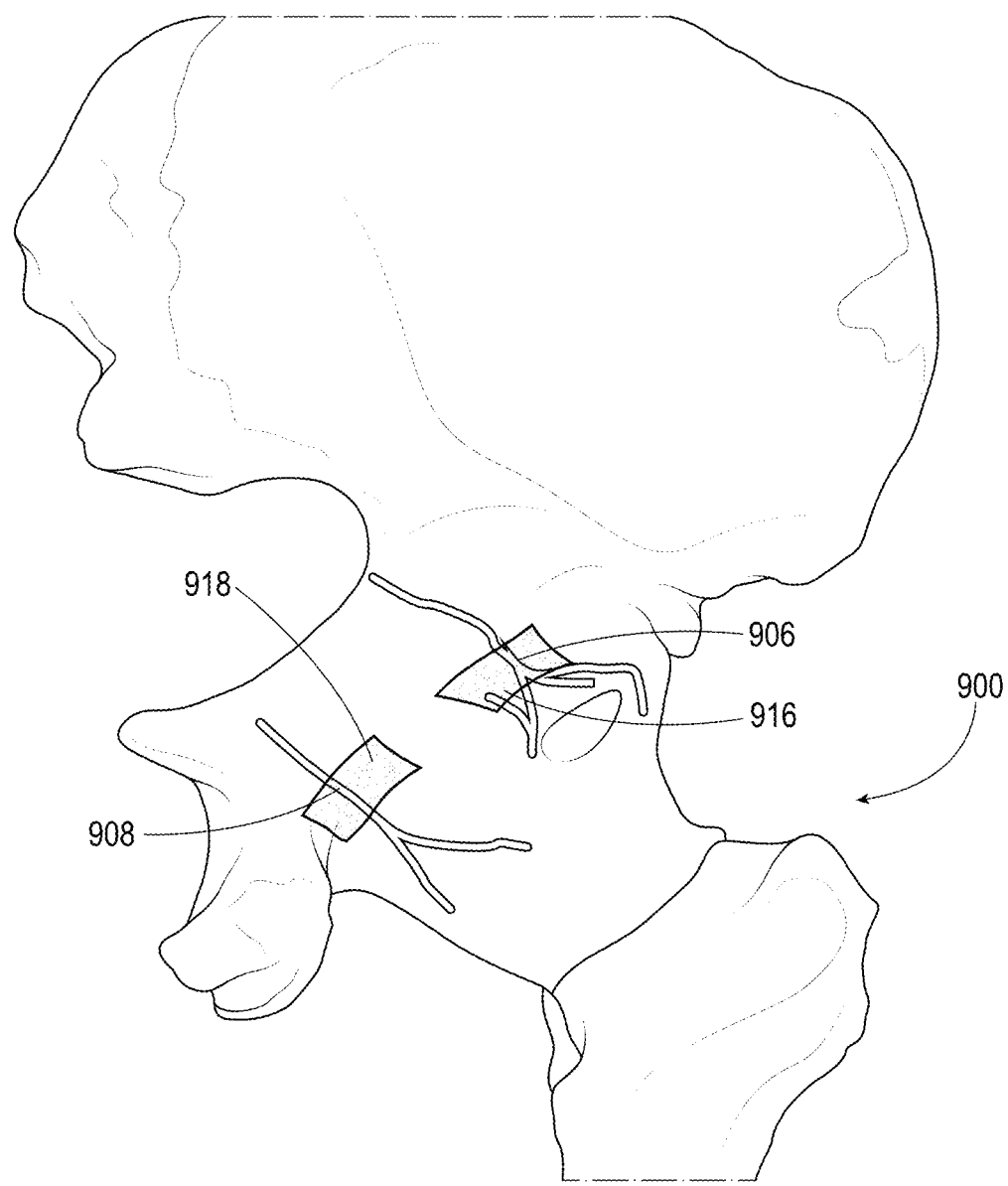

Turning to FIGS. 21 and 22, pain at the hip joint 900 can be treated by targeting for cauterization and transection with techniques described herein the sensory nerves that innervate the hip joint immediately outside the hip joint. The procedure is carried out to target at least one of, and preferably all of, the following nerves: an articular branch of the femoral nerve 902, an articular branch of the obturator nerve 904, an articular branch of the superior gluteal nerve 906, and an articular branch of the nerve to the quadratus femoris 908. In an embodiment, the nerves innervating the hip joint are targeted as follows. The articular branch of the femoral nerve 902 is cauterized in a burn region 912 along and above the bone inferomedial to the anterior inferior iliac spine along the superior rim of the acetabulum exterior to the joint capsule. The articular branch of the obturator nerve 904 is cauterized in a burn region 9114 along and above the bone surface at the junction of the pubic and iliac bones in the region of the "teardrop" as well as the bone surface immediately inferior to the teardrop. The articular branch of the superior gluteal nerve 906 is cauterized in burn region 916 posterior along the acetabulum proximal to the joint labrum. The articular branch of the nerve 908 to the quadratus femoris is cauterized in burn region 918 posterior along the acetabulum proximal to the joint labrum.

Knee Joint Rhizotomy

Figure 23:
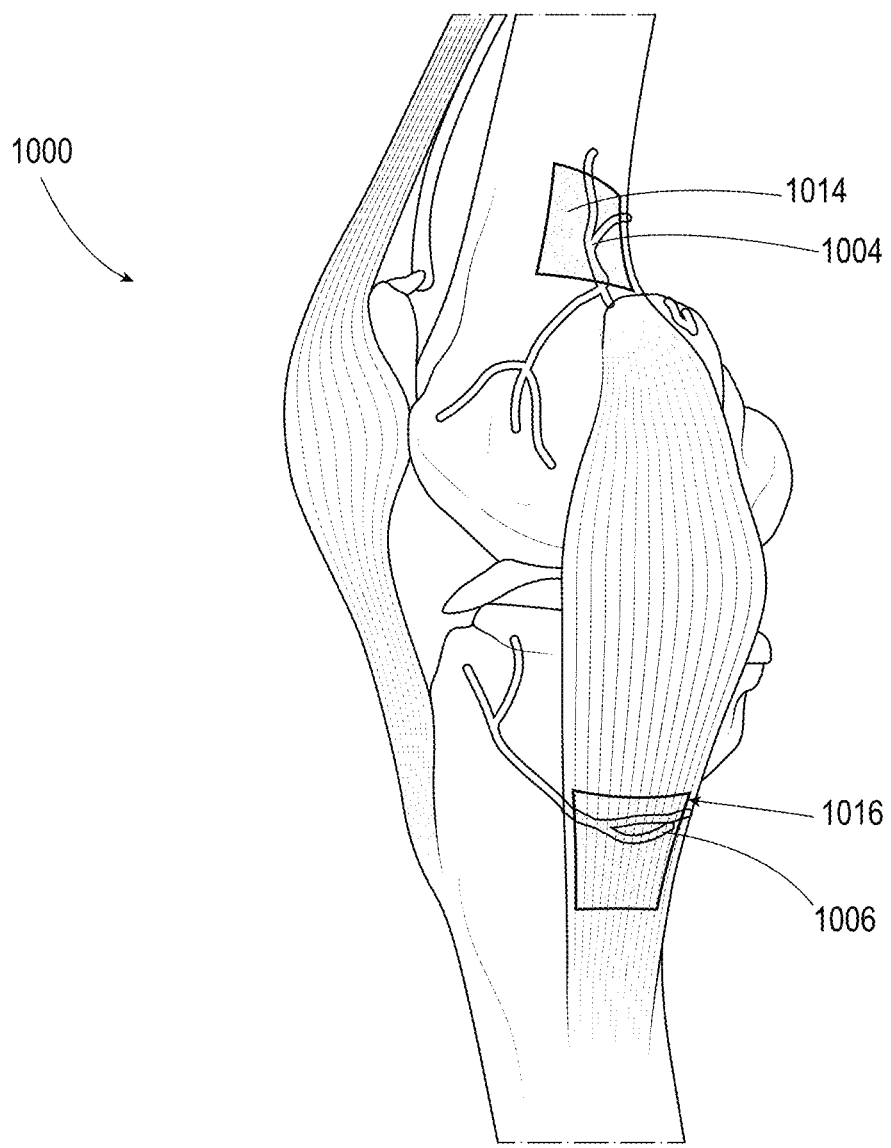
FIGS. 23, 24 and 25 illustrate target anatomy and the areas of treatment for a wanded cautery rhizotomy procedure on a knee joint, with FIG. 23 illustrating medio-posterior view of a left knee joint, FIG. 24 illustrating an anterior view of a left knee joint, and FIG. 25 illustrating a lateral-anterior view of a left knee joint.
Figure 24:
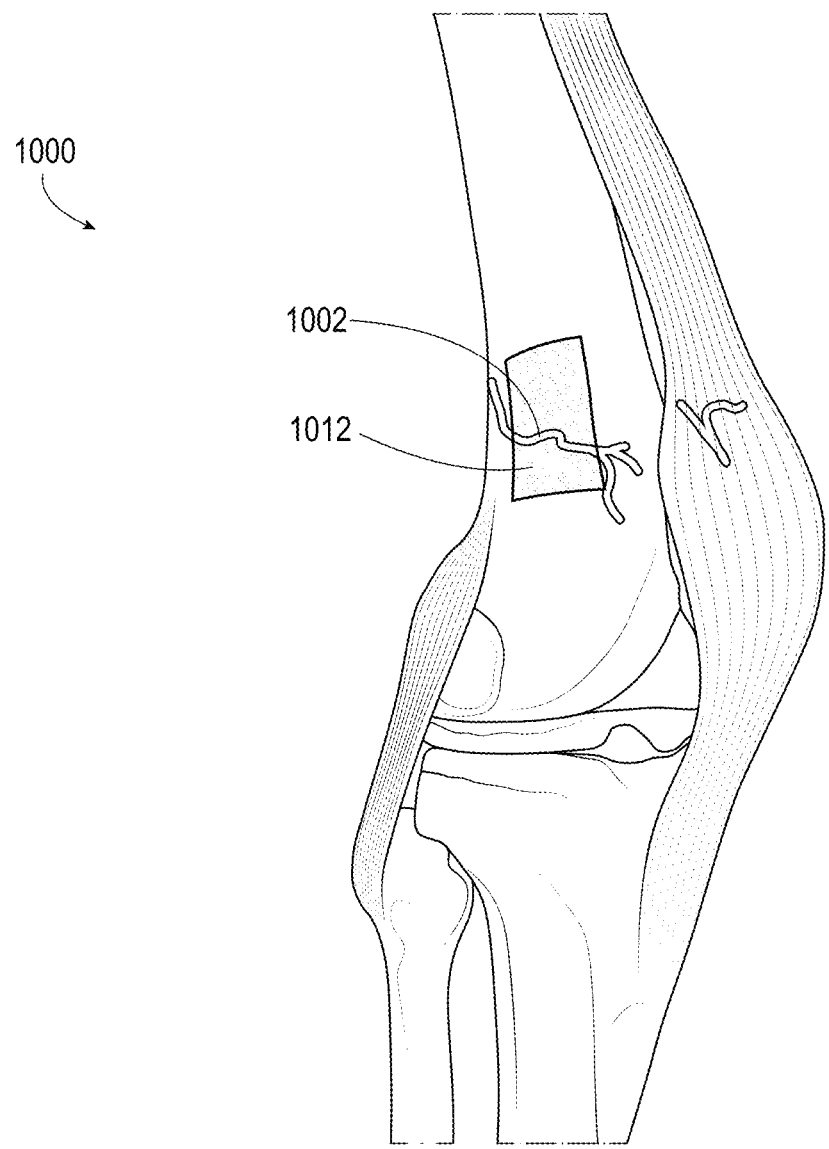
Figure 25:
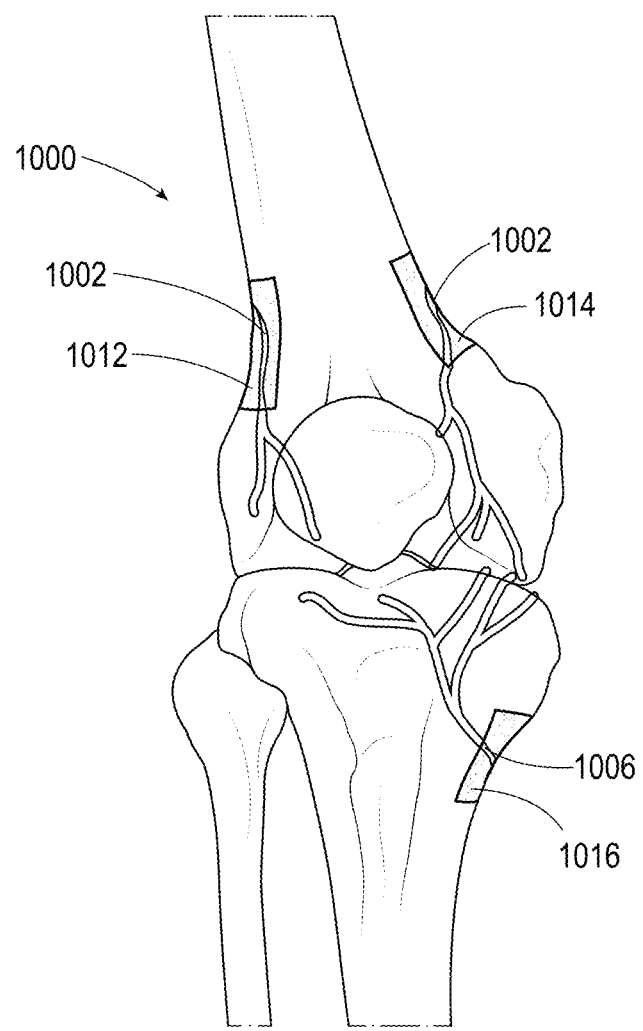

Turning to FIGS. 23 through 25, pain at the knee joint 1000 can be treated by targeting for cauterization and transection with techniques described herein the sensory nerves that innervate the knee joint immediately outside the knee joint. The procedure is carried out to target at least one of, and preferably all of, the following nerves: a superolateral genicular nerve 1002, a superomedial genicular nerve 1004, and an inferomedial genicular nerve 1006. The superolateral genicular nerve 1002 is cauterized in a burn region 1012 at a junction of a femoral shaft and a lateral femoral condyle. The superomedial genicular nerve 1004 is cauterized in region 1014 at a junction of the femoral shaft and a medial femoral condyle. The inferomedial genicular nerve 1006 is cauterized in burn region 1016 at a location between a tibial shaft and a medial tibial tubercle.

The above description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventor(s) also contemplate examples in which only those elements shown or described are provided. Moreover, the present inventor(s) also contemplate examples using combinations or permutations of those elements shown or described. Where numbers are qualified herein with "approximately", such qualified numbers include the referenced value and variations with ±10%.

As such, when it is taught that a group of sensory nerves be cauterized to eliminate pain at a joint, it is recognized and within the scope of the methods herein, that fewer than all of the nerves may be cauterized (where one or more nerves are not active in signaling pain to the patient) or additional sensory nerves may be cauterized, and all such configurations are within the scope described herein.

The above description is intended to be illustrative, and not restrictive. For example, the above-described examples (or one or more aspects thereof) may be used in combination with each other. Other embodiments may be used, such as by one of ordinary skill in the art upon reviewing the above description. While a RF cautery device is described for use in the treatment, it is appreciated that such device includes all suitable plasmacautery and electrocautery devices capable of performing as required for the methods described herein. While the methods have been discussed with respect to ablating and transecting sensory nerves extending adjacent joints to treat chronic joint pain, it is appreciated that with the tools described, wanded cautery procedures can be used to treat sensory nerves extending at regions separated from joints. Moreover, such tools and wanded cautery procedures can be used to ablate and transect other nerves extending along a boney surface to treat appropriate conditions. In addition, the above description has been discussed in application to treat conditions of the human body, it is appreciated that the devices and techniques can also be applied to treat conditions on non-human animals. For example, the systems and methods can be applied to treat chronic pain and other conditions of the joints in a variety of mammals, including, but not limited to, in equine, canine and feline applications. The scope of the invention should be determined with reference to the appended claims, along with the full scope of equivalents to which such claims are entitled.

What is claimed is:

1. A method of performing a rhizotomy on at least one target sensory nerve extending along one or more boney outer surfaces that innervate a joint of a body of a patient, the method comprising:
   providing a surgical probe having a distal tip, the distal tip of the surgical probe suitable for performing a percutaneous procedure;
   creating an incision in the body of the patient;
   directing the distal tip of the probe through the incision;
   navigating the distal tip of the probe via medical imaging to a first location on a first boney outer surface adjacent a first target sensory nerve;
   activating the probe;
   while activating the probe, moving the distal tip of the probe in a plurality of directions over a first surface area along the first boney outer surface to interrupt function of the target sensory nerve; and
   deactivating the probe,
   wherein the distal tip of the probe is sufficiently stiff to resist deformation when moved over the surface area.

2. The method of claim 1, wherein the target sensory nerve is a nerve that runs along the boney outer surface, and the moving the distal tip includes wanding the distal tip along the boney outer surface.

3. The method of claim 2, wherein the moving also includes wanding the distal tip above the boney outer surface.

4. The method of claim 1, wherein interrupting function of the target sensory nerve includes cauterizing of the target sensory nerve.

5. The method of claim 1, wherein interrupting function of the target sensory nerve includes transecting of the target sensory nerve.

6. The method of claim 1, wherein medical imaging includes fluoroscopy.

7. The method of claim 1, wherein activating the probe includes delivering energy from the probe to the target sensory nerve.

8. The method of claim 7, wherein delivering energy comprises delivering radio frequency energy.

9. The method of claim 7, wherein the energy is delivered to the target sensory nerve for a time period in a range from 3 seconds to 10 seconds.

10. The method of claim 1, further comprising:
delivering medication to the target sensory nerve prior to interrupting function of the nerve.

11. The method of claim 10, wherein the medicine comprises at least one of a local anesthetic and an anti-inflammatory medicine.

12. The method of claim 10, wherein the medicine comprises at least one of novocaine, bupivacaine, and methylprednisolone.

13. The method of claim 1, wherein the probe includes a lumen, and the medicine is delivered through the lumen.

14. The method of claim 1, wherein the boney outer surface includes a vertebra of a spine.

15. The method of claim 14, wherein the target sensory nerve is a medial branch of a dorsal ramus.

16. The method of claim 15, wherein the vertebra has a transverse process and a pedicle, and moving the distal tip includes wanding the distal tip along the transverse process to the pedicle.

17. The method of claim 1, wherein the boney outer surface includes the sacrum, and the target sensory nerve is a sensory nerve that runs along the sacrum.

18. The method of claim 1, wherein the joint is a sacroiliac joint.

19. The method of claim 1, wherein the joint is a shoulder joint.

20. The method of claim 1, wherein the joint is a hip joint.

21. The method of claim 1, wherein the joint is a knee joint.

22. The method of claim 1, wherein the surface area is greater than 10 mm$^2$.

23. The method of claim 1, further comprising:
after deactivating the probe, moving the distal end of the probe to another location;
again delivering energy from the distal tip of the probe; and
while again delivering energy, moving the distal tip of the probe in a plurality of directions to direct the energy over a second surface area distinct from the first surface area to interrupt function of a second target sensory nerve.

24. The method of claim 23, wherein the probe is moved to another location without removing the distal tip from the incision.

25. The method of claim 23, wherein interrupting function of the first target nerve transects the first target nerve, and the interrupting function of the second target nerve transects the second target nerve.

26. A method of performing a rhizotomy on a target sensory nerve that innervates a joint of a body of a patient, the target sensory nerve extending along a boney outer surface, the method comprising:
creating an incision in the body of the patient;
directing a distal tip of a percutaneously-insertable surgical probe through the incision;
navigating the distal tip of the probe via medical imaging to a location on the boney outer surface adjacent the target sensory nerve;
delivering medication to the target sensory nerve; then
activating the distal tip of the probe to delivery energy to the target sensory nerve;
while activating the distal tip of the probe, moving the distal tip of the probe over a surface area along the boney outer surface to interrupt function of the target sensory nerve.

27. The method of claim 26, wherein the probe is provided with a lumen, and the medication is delivered through the lumen.

28. The method of claim 26, wherein the medication includes at least one of a local anesthetic and an anti-inflammatory medicine.

29. The method of claim 28, wherein the medication comprises at least one of novocaine, bupivacaine, and methylprednisolone.

* * * * *